US008404444B2

(12) United States Patent
Zhang et al.

(10) Patent No.: US 8,404,444 B2
(45) Date of Patent: Mar. 26, 2013

(54) METHOD FOR PREDICTING THE LEVEL OF DAMAGE TO CELLS BY MEASURING FREE CIRCULATING ALU NUCLEIC ACID

(75) Inventors: Lurong Zhang, Gainesville, FL (US); Paul Okunieff, Gainesville, FL (US); Lulu Zhang, Gainsville, FL (US); Aiguo Zhang, Fremont, CA (US)

(73) Assignee: Diacarta LLC, Hayward, CA (US)

( * ) Notice: Subject to any disclaimer, the term of this patent is extended or adjusted under 35 U.S.C. 154(b) by 750 days.

(21) Appl. No.: 12/392,989

(22) Filed: Feb. 25, 2009

(65) Prior Publication Data

US 2011/0183326 A1  Jul. 28, 2011

(51) Int. Cl.
 *C12Q 1/68* (2006.01)
(52) U.S. Cl. .................................... 435/6.11; 435/6.1
(58) Field of Classification Search .................. None
 See application file for complete search history.

(56) References Cited

U.S. PATENT DOCUMENTS

| | | | |
|---|---|---|---|
| 7,008,768 B1 * | 3/2006 | Fornace et al. ............. | 435/6.11 |
| 2006/0145091 A1 * | 7/2006 | Patel .......................... | 250/474.1 |
| 2007/0015188 A1 * | 1/2007 | Luo et al. .................... | 435/6 |
| 2007/0166726 A1 * | 7/2007 | Fornace et al. .............. | 435/6 |
| 2009/0214467 A1 * | 8/2009 | Shakhov et al. ............. | 424/85.2 |

OTHER PUBLICATIONS

Vasilyeva, I.N. Annals NY Acad Sci. 2001. 945:221-228.*
Costello et al (International Congress Series. 2006. 1288: 753-755.*
Kostyuk et al. Radiatsionnaia Biologiia. Jan. 2008. 48(1): 5-13.*
Antonatos, et al. Cell-free DNA levels as a prognostic marker in acute myocardial infarction. Ann. N.Y. Acad. Sci. 1075:278-281 (2006).
Arias, et al. Plasma DNA restoration for PCR applications. J. Clin. Pathol. 2007. 60:952-954 (2006).
Bagul, et al. Quantatve analysis of plasma DNA in severe acute pancreatitis. JOP J. Pancreas 7(6):602-607 (2006).
Batzer, et al. ALU repeats and human genomic diversity. Nature Reviews (Genetics), 3: 370-380 (May 2002).
Boni, et al. Free circulating DNA as possible tumour marker in colorectal cancer. Surg. Oncology 16:529-531 (2007).
Capizzi, et al. Quantfiaton of free plasma DNA before and after chemotherapy in patents with advanced epithelial ovarian cancer. Diagn. Mol. Pathol. 17(1): 34-38 (Mar. 2008).
Chan, et al. Hypermethylated RASSFIA in maternal plasma: a universal fetal DNA marker that improves the reliability of noninvasive prenatal diagnosis. Clinical Chem. 52(12): 2211-2218 (2006).
Chen, et al. Circulation DNA: biological implications for cancer metastasis and immunology. Medical Hypotheses 65: 956-961 (2005).
Clausen, et al. Improvement in fetal DNA extraction from maternal plasma. Evaluation of the NucliSens Magnetic Extraction system and the QIAamp DSP virus kit in comparison with the QIAamp DNA blood mini kit. Prenat. Diagn 27: 6-10 (2007).
Finning, et al. Fetal genotyping for the cell K(Kell) and Rh, C, c and E blood groups on cell-free fetal DNA in maternal plasma. Transfusion. 47:2126-2133 (Nov. 2007).
Fox, et al. Quantficaton of circulating cell-free plasma DNA and endothelial gene RNA in patents with burns and relation to acute thermal injury. Burns (2008). 34(6):809-816 EPub.
Frattini, et al. Quantitative and qualitative charcterization of plasma DNA identifies primary and rucurrent colorectal cancer. Cancer Letters. 263:170-181 (2008).
Frattini, et al. Quantitative analysis of plasma DNA in colorectal cancer patients. Ann. N.Y. Acad. Sci. 1075: 185-190 (2006).
Gormally, et al. Amount of DNA in plasma and cancer risk: a prospective study. Int. J. Cancer. 111:746-749 (2004).
Gormally, et al. Circulating free DNA in plasma or serum as biomarker of carcinogenesis: practical aspects and biological significance. Mutation Research 635:105-117 (2007).
Hampton. Methods to detect circulating tumor DNA may help early diagnosis of cancer. JAMA. 298(17):1993-1994 (Nov. 7, 2007).
Kamat, et al. Quantification of total plasma cell-free DNA in ovarian cancer using real-time PCR. Ann. N.Y. Acad. Sci. 1075: 230-234 (2006).
Kamat,et al. Circulating cell free DNA: a novel biomarker for response to therapy in ovarian carcinoma. Cancer Biol. & Therapy 5(10):1369-1374 (Oct. 2006).
Kelly, et al. A global role for Fis in the transcriptional control of metabolism and type III secretion in *Salmonella enterica* serovar typhimurium. Microbiology 150:2037-2053 (2004).
Langford, et al. Plasma levels of cell-free apoptotic DNA ladders and gamma-glutamyltranspeptidase (GGT) in diabetic children. Expt. Biol. Med. 232(9)1160-1169, 2007.
Li, et al. Noninvasive genotyping fetal Kell blood group (KEL1) using cell-free fetal DNA in maternal plasma by MALDI-TOF mass spectrometry. Prenatal Diag. 28: 203-208 (2008).
Lui, et al. Circulating DNA in plasma and serum: biology, preanalytical issues and diagnostic applications. Clin. Chem. Lab. Med. 40(10):962-968 (2002).
Majer, et al. Matenal urine or prenatal diagnosis—an analysis of cell-free fetal DNA in maternal urine and plasma in the third trimester. Prenat. Diagn. 27: 1219-1223 (2007).
Page, et al. The importance of careful blood processing in isolation of cell-free DNA. Ann. N.Y. Acad. Sci. 1075: 313-317 (2006).
Perego, et al. Concentration and micosatellite status of plasma DNA for monitoring patients with renal carcinoma. Eur. J. Cancer 44(7):1039-1047 (2008). EPub.
Rhodes, et al. Plasma DNA concentration as a predictor of mortality and sepsis in critically ill patients. Critical Care 10(2):60 (2006). EPub.
Saukkonen, et al. Association of cell-free plasma DNA with hospital mortality and organ dysfunction in intensive care unit patients. Intensive Care Med. 33:1624-1627 (2007).

(Continued)

*Primary Examiner* — Carla Myers
(74) *Attorney, Agent, or Firm* — James S. Keddie; Bozicevic, Field & Francis, LLP

(57) ABSTRACT

This invention relates generally to methods for detecting cell damage as a consequence of pathophysiological or traumatic insults such as in a nuclear accident, bioterror attack, tumorigenesis, infections or in individuals with cardiovascular disease.

12 Claims, 9 Drawing Sheets

OTHER PUBLICATIONS

Teare, et al. Genomic tests: unreliable for cancer? A focus on circulating DNA and lung cancer. Expert Rev. Mol. Diagn. 7(6):699-702 (2007).

Tungwiwat et al. Application of maternal plasma DNA analysis for noninvasve prenatal dignosis of Hb E-β-thalassemia. Transl. Res. 150(5):319-325 (2007). EPub.

Umetani, et al. Increased integrity of free circulating DNA in sera of patients with colorectal or periampullary cancer: direct quantitative PCR for ALU repeats. Clinical Chem 52:(6) 1062-1069 (2006).

Umetani, et al. Higher amount of free ciculating DNA in serum than in plasma is not mainly caused by contaminated extraneous DNA during separation. Ann. N.Y. Acad. Sci. 1075:299-307 (2006).

Van Der Vaart, et al. The origin of circulating free DNA. Clinical Chem. 53(12):2215 Letters (2007).

Vasavda, et al. Cirulating DNA: a potential marker of sickle cell crisis. British J. of Haematology 139:331-336 (2007).

Vermeersch, et al. MALDI-TOF spectometry compared with real-time PCR for detection of fetal cell-free DNA in maternal plasma. Clin. Chem. 52(12):2311-2312 Letters (2006).

Widschwendter, et al. Circulating methylated DNA: a new generation of tumor markers. Cin. Cancer Res. 12 (24):7205-7208 (Dec. 15, 2006).

Wong, et al. Cell-free DNA and RNA in pasma as new tools for moecuar diagnostics. Expert Rev. Mol. Diagn. 3(6) 785-797 (2003).

Yurgel, et al. Role of plasma DNA as a predictive marker of fatal outcome following severe head injury in males. J. Neurotrauma 24(7):1172-1181 (2007).

Zeerleder. The struggle to detect circulating DNA. Critical Care 10(3):142 (2006) EPub.

Deligezer, et al., "Size distribution of circulating cell-free DNA in sera of breast cancer patients in the course of adjuvant chemotherapy", Clin Chem Lab Med, 2008, 46:311-7.

El-Shazly, et al., "Evaluation of serum DNA integrity as a screening and prognostic tool in patients with hepatitis C virus-related hepatocellular carcinoma", Int J Biol Markers, 2010, 25:79-86.

Park, et al., "Quantitative analysis of cell-free DNA in the plasma of gastric cancer patients", Oncol Lett, 2012, 3:921-926.

* cited by examiner

A.

B.

```
                        SEQUENCE LISTING

<160> NUMBER OF SEQ ID NOS: 84

<210> SEQ ID NO 1
<211> LENGTH: 201
<212> TYPE: DNA
<213> ORGANISM: Homo sapiens

<400> SEQUENCE: 1
agaccatcct ggctaacacg gtgaaacccc gtctctacta aaaatacaaa aaattagccg      60
ggcgtggtgg cgggcgcctg tagtcccagc tactcgggag gctgaggcag gagaatggcg    120
tgaacccggg aggcggagct tgcagtgagc cgagatcgcg ccactgcact ccagcctggg    180
cgacagagcg agactccgtc t                                              201

<210> SEQ ID NO 2
<211> LENGTH: 201
<212> TYPE: DNA
<213> ORGANISM: Homo sapiens

<400> SEQUENCE: 2
agaccatcct ggctaacacg gtgaaacccc gtctctacta aaaatacaaa aaattagccg      60
ggcgtggtgg cgggcgcctg tagtcccagc tactcgggag gctgaggcag gagaatggcg    120
tgaacccggg aggcggagct tgcagtgagc cgagatcgcg ccactgcact ccagcctggg    180
cgacagagcg agactccgtc t                                              201

<210> SEQ ID NO 3
<211> LENGTH: 413
<212> TYPE: DNA
<213> ORGANISM: Homo sapiens

<400> SEQUENCE: 3
atgccagagt ctcgttcgtt atcggaatta accagacaaa tcgctccacc aactaagaac      60
ggccatgcac caccaccac ggaatcgaga aagagctatc aatctgtcaa tcctgtccgt    120
```

-continued

```
gtccgggccg ggtgaggttt cccgtgttga gtcaaattaa gccgcaggct ccactcctgg      180
tggtgccctt ccgtcaattc ctttaagttt cagctttgca accatactcc ccccggaacc      240
caaagacttt ggtttcccgg aagctgcccg gcgggtcatg ggaataacgc cgccgcatcg      300
ccggtcggca tcgtttatgg tcggaactac gacggtatct gatcgtcttc gaacctccga      360
ctttcgttct tgattaatga aaacattctt ggcaaatgct ttcgctctgg tcc             413
```

<210> SEQ ID NO 4
<211> LENGTH: 474
<212> TYPE: DNA
<213> ORGANISM: Homo sapiens

<400> SEQUENCE: 4

```
cgttcagtca taatcccaca gatggtagct tcgccccatt ggctcctcag ccaagcacat       60
acaccaaatg tctgaacctg cggttcctct cgtactgagc aggattacca tggcaacaac      120
acatcatcag tagggtaaaa ctaacctgtc tcacgacggt ctaaacccag ctcacgttcc      180
ctattagtgg gtgaacaatc caacgcttgg cgaattctgc ttcacaatga taggaagagc      240
cgacatcgaa ggatcaaaaa gcgacgtcgc tatgaacgct tggccgccac aagccagtta      300
tccctgtggt aactttctg acacctcctg cttaaaaccc aaaaggtcag aaggatcgtg       360
aggccccgct ttcacggtct gtattcgtac tgaaaatcaa gatcaagcga gcttttgccc      420
ttctgctcca cgggaggttt ctgtcctccc tgagctcgcc ttaggacacc tgcg            474
```

<210> SEQ ID NO 5
<211> LENGTH: 6
<212> TYPE: DNA
<213> ORGANISM: Homo sapiens

<400> SEQUENCE: 5

```
ttaggg                                                                   6
```

<210> SEQ ID NO 6
<211> LENGTH: 8
<212> TYPE: DNA
<213> ORGANISM: Homo sapiens

<400> SEQUENCE: 6

```
ttttgggg                                                                 8
```

<210> SEQ ID NO 7
<211> LENGTH: 45
<212> TYPE: DNA
<213> ORGANISM: Artificial Sequence
<220> FEATURE:
<223> OTHER INFORMATION: Capture extender sequence

<400> SEQUENCE: 7

```
attttagta gagacggggt ttcatttttc tcttggaaag aaagt                        45
```

<210> SEQ ID NO 8
<211> LENGTH: 40
<212> TYPE: DNA
<213> ORGANISM: Artificial Sequence
<220> FEATURE:
<223> OTHER INFORMATION: Capture extender sequence

<400> SEQUENCE: 8

```
cgcccggcta attttttgtt ttttctcttg gaaagaaagt                              40
```

-continued

<210> SEQ ID NO 9
<211> LENGTH: 38
<212> TYPE: DNA
<213> ORGANISM: Artificial Sequence
<220> FEATURE:
<223> OTHER INFORMATION: Capture extender sequence

<400> SEQUENCE: 9
cgcctcccgg gttcacgttt ttctcttgga aagaaagt                                38

<210> SEQ ID NO 10
<211> LENGTH: 38
<212> TYPE: DNA
<213> ORGANISM: Artificial Sequence
<220> FEATURE:
<223> OTHER INFORMATION: Capture extender sequence

<400> SEQUENCE: 10
ggagtgcagt ggcgcgattt ttctcttgga aagaaagt                                38

<210> SEQ ID NO 11
<211> LENGTH: 39
<212> TYPE: DNA
<213> ORGANISM: Artificial Sequence
<220> FEATURE:
<223> OTHER INFORMATION: Capture extender sequence

<400> SEQUENCE: 11
cgctctgtcg cccaggcttt tttctcttgg aaagaaagt                               39

<210> SEQ ID NO 12
<211> LENGTH: 55
<212> TYPE: DNA
<213> ORGANISM: Artificial Sequence
<220> FEATURE:
<223> OTHER INFORMATION: Capture extender sequence

<400> SEQUENCE: 12
cgcccggcta attttttgta tttttagtag agactttttc tcttggaaag aaagt             55

<210> SEQ ID NO 13
<211> LENGTH: 48
<212> TYPE: DNA
<213> ORGANISM: Artificial Sequence
<220> FEATURE:
<223> OTHER INFORMATION: Capture extender sequence

<400> SEQUENCE: 13
tctcctgcct cagcctcccg agtagctttt ttctcttgga aagaaagt                     48

<210> SEQ ID NO 14
<211> LENGTH: 42
<212> TYPE: DNA
<213> ORGANISM: Artificial Sequence
<220> FEATURE:
<223> OTHER INFORMATION: Capture extender sequence

<400> SEQUENCE: 14
cgcctcccgg gttcacgcca tttttctct tggaaagaaa gt                            42

<210> SEQ ID NO 15
<211> LENGTH: 45
<212> TYPE: DNA
<213> ORGANISM: Artificial Sequence
<220> FEATURE:
<223> OTHER INFORMATION: Capture extender sequence

<400> SEQUENCE: 15

```
gtcgcccagg ctggagtgca gtggttttc tcttggaaag aaagt              45

<210> SEQ ID NO 16
<211> LENGTH: 42
<212> TYPE: DNA
<213> ORGANISM: Artificial Sequence
<220> FEATURE:
<223> OTHER INFORMATION: Capture extender sequence

<400> SEQUENCE: 16
caaagtgctg ggattacagg cttttctct tggaaagaaa gt                  42

<210> SEQ ID NO 17
<211> LENGTH: 45
<212> TYPE: DNA
<213> ORGANISM: Artificial Sequence
<220> FEATURE:
<223> OTHER INFORMATION: Capture extender sequence

<400> SEQUENCE: 17
tttcattata ttggtcaggc tggttttttc tcttggaaag aaagt              45

<210> SEQ ID NO 18
<211> LENGTH: 40
<212> TYPE: DNA
<213> ORGANISM: Artificial Sequence
<220> FEATURE:
<223> OTHER INFORMATION: Capture extender sequence

<400> SEQUENCE: 18
gctgggatta caggcaccct ttttctcttg gaaagaaagt                    40

<210> SEQ ID NO 19
<211> LENGTH: 39
<212> TYPE: DNA
<213> ORGANISM: Artificial Sequence
<220> FEATURE:
<223> OTHER INFORMATION: Capture extender sequence

<400> SEQUENCE: 19
cgctctgtcg cccaggcttt ttctcttgg aaagaaagt                      39

<210> SEQ ID NO 20
<211> LENGTH: 42
<212> TYPE: DNA
<213> ORGANISM: Artificial Sequence
<220> FEATURE:
<223> OTHER INFORMATION: Capture extender sequence

<400> SEQUENCE: 20
catggccgtt cttagttggt gttttctct tggaaagaaa gt                  42

<210> SEQ ID NO 21
<211> LENGTH: 38
<212> TYPE: DNA
<213> ORGANISM: Artificial Sequence
<220> FEATURE:
<223> OTHER INFORMATION: Capture extender sequence

<400> SEQUENCE: 21
ggcccggaca cggacagttt ttctcttgga agaaagt                       38

<210> SEQ ID NO 22
<211> LENGTH: 45
<212> TYPE: DNA
<213> ORGANISM: Artificial Sequence
```

-continued

<220> FEATURE:
<223> OTHER INFORMATION: Capture extender sequence

<400> SEQUENCE: 22
tgaaacttaa aggaattgac ggaattttc tcttggaaag aaagt        45

<210> SEQ ID NO 23
<211> LENGTH: 38
<212> TYPE: DNA
<213> ORGANISM: Artificial Sequence
<220> FEATURE:
<223> OTHER INFORMATION: Capture extender sequence

<400> SEQUENCE: 23
gggcagcttc cgggaaattt ttctcttgga aagaaagt        38

<210> SEQ ID NO 24
<211> LENGTH: 40
<212> TYPE: DNA
<213> ORGANISM: Artificial Sequence
<220> FEATURE:
<223> OTHER INFORMATION: Capture extender sequence

<400> SEQUENCE: 24
gttattccca tgacccgcct ttttctcttg gaaagaaagt        40

<210> SEQ ID NO 25
<211> LENGTH: 42
<212> TYPE: DNA
<213> ORGANISM: Artificial Sequence
<220> FEATURE:
<223> OTHER INFORMATION: Capture extender sequence

<400> SEQUENCE: 25
cgaaagtcgg aggttcgaag atttttctct tggaaagaaa gt        42

<210> SEQ ID NO 26
<211> LENGTH: 43
<212> TYPE: DNA
<213> ORGANISM: Artificial Sequence
<220> FEATURE:
<223> OTHER INFORMATION: Capture extender sequence

<400> SEQUENCE: 26
ggtgtatgtg cttggctgag gattttctc ttggaaagaa agt        43

<210> SEQ ID NO 27
<211> LENGTH: 42
<212> TYPE: DNA
<213> ORGANISM: Artificial Sequence
<220> FEATURE:
<223> OTHER INFORMATION: Capture extender sequence

<400> SEQUENCE: 27
ggaacgtgag ctgggtttag attttctct tggaaagaaa gt        42

<210> SEQ ID NO 28
<211> LENGTH: 42
<212> TYPE: DNA
<213> ORGANISM: Artificial Sequence
<220> FEATURE:
<223> OTHER INFORMATION: Capture extender sequence

<400> SEQUENCE: 28
cgacgtcgct ttttgatcct ttttttctct tggaaagaaa gt        42

```
<210> SEQ ID NO 29
<211> LENGTH: 39
<212> TYPE: DNA
<213> ORGANISM: Artificial Sequence
<220> FEATURE:
<223> OTHER INFORMATION: Capture extender sequence

<400> SEQUENCE: 29
gcggccaagc gttcatagtt tttctcttgg aaagaaagt                                  39

<210> SEQ ID NO 30
<211> LENGTH: 43
<212> TYPE: DNA
<213> ORGANISM: Artificial Sequence
<220> FEATURE:
<223> OTHER INFORMATION: Capture extender sequence

<400> SEQUENCE: 30
tccttctgac cttttgggtt ttttttctc ttggaaagaa agt                              43

<210> SEQ ID NO 31
<211> LENGTH: 39
<212> TYPE: DNA
<213> ORGANISM: Artificial Sequence
<220> FEATURE:
<223> OTHER INFORMATION: Capture extender sequence

<400> SEQUENCE: 31
tcccgtggag cagaagggtt tttctcttgg aaagaaagt                                  39

<210> SEQ ID NO 32
<211> LENGTH: 48
<212> TYPE: DNA
<213> ORGANISM: Artificial Sequence
<220> FEATURE:
<223> OTHER INFORMATION: Label extender sequence

<400> SEQUENCE: 32
ccgtgttagc caggatggtc tttttctga gtcaaagcat gaagttac                         48

<210> SEQ ID NO 33
<211> LENGTH: 48
<212> TYPE: DNA
<213> ORGANISM: Artificial Sequence
<220> FEATURE:
<223> OTHER INFORMATION: Label extender sequence

<400> SEQUENCE: 33
tcccgagtag ctgggactac attttctga gtcaaagcat gaagttac                         48

<210> SEQ ID NO 34
<211> LENGTH: 46
<212> TYPE: DNA
<213> ORGANISM: Artificial Sequence
<220> FEATURE:
<223> OTHER INFORMATION: Label extender sequence

<400> SEQUENCE: 34
ccattctcct gcctcagcct ttttctgagt caaagcatga agttac                          46

<210> SEQ ID NO 35
<211> LENGTH: 47
<212> TYPE: DNA
<213> ORGANISM: Artificial Sequence
<220> FEATURE:
<223> OTHER INFORMATION: Label extender sequence

<400> SEQUENCE: 35
```
tctcggctca ctgcaagctc tttttctgag tcaaagcatg aagttac                  47

<210> SEQ ID NO 36
<211> LENGTH: 57
<212> TYPE: DNA
<213> ORGANISM: Artificial Sequence
<220> FEATURE:
<223> OTHER INFORMATION: Label extender sequence

<400> SEQUENCE: 36
ggggtttcac cgtgttagcc aggatggtct tttttctgag tcaaagcatg aagttac       57

<210> SEQ ID NO 37
<211> LENGTH: 50
<212> TYPE: DNA
<213> ORGANISM: Artificial Sequence
<220> FEATURE:
<223> OTHER INFORMATION: Label extender sequence

<400> SEQUENCE: 37
gggactacag gcgcccgcca ccattttttct gagtcaaagc atgaagttac              50

<210> SEQ ID NO 38
<211> LENGTH: 52
<212> TYPE: DNA
<213> ORGANISM: Artificial Sequence
<220> FEATURE:
<223> OTHER INFORMATION: Label extender sequence

<400> SEQUENCE: 38
cgcgatctcg gctcactgca agctcttttt ctgagtcaaa gcatgaagtt ac            52

<210> SEQ ID NO 39
<211> LENGTH: 45
<212> TYPE: DNA
<213> ORGANISM: Artificial Sequence
<220> FEATURE:
<223> OTHER INFORMATION: Label extender sequence

<400> SEQUENCE: 39
ccaccagctt cggcctcctt tttctgagtc aaagcatgaa gttac                    45

<210> SEQ ID NO 40
<211> LENGTH: 51
<212> TYPE: DNA
<213> ORGANISM: Artificial Sequence
<220> FEATURE:
<223> OTHER INFORMATION: Label extender sequence

<400> SEQUENCE: 40
ctcaaactcc tgacctcaag tgattttttc tgagtcaaag catgaagtta c             51

<210> SEQ ID NO 41
<211> LENGTH: 53
<212> TYPE: DNA
<213> ORGANISM: Artificial Sequence
<220> FEATURE:
<223> OTHER INFORMATION: Label extender sequence

<400> SEQUENCE: 41
tttttgtatt tttagtagag atggggtttt tctgagtcaa agcatgaagt tac           53

<210> SEQ ID NO 42
<211> LENGTH: 45
<212> TYPE: DNA
<213> ORGANISM: Artificial Sequence
<220> FEATURE:
<223> OTHER INFORMATION: Label extender sequence

<400> SEQUENCE: 42
gccaccacgc ccagctaatt tttctgagtc aaagcatgaa gttac          45

<210> SEQ ID NO 43
<211> LENGTH: 47
<212> TYPE: DNA
<213> ORGANISM: Artificial Sequence
<220> FEATURE:
<223> OTHER INFORMATION: Label extender sequence

<400> SEQUENCE: 43
ctgcctcagc ctcccaagta tttttctgag tcaaagcatg aagttac          47

<210> SEQ ID NO 44
<211> LENGTH: 47
<212> TYPE: DNA
<213> ORGANISM: Artificial Sequence
<220> FEATURE:
<223> OTHER INFORMATION: Label extender sequence

<400> SEQUENCE: 44
cccaggttca agcgattctc tttttctgag tcaaagcatg aagttac          47

<210> SEQ ID NO 45
<211> LENGTH: 42
<212> TYPE: DNA
<213> ORGANISM: Artificial Sequence
<220> FEATURE:
<223> OTHER INFORMATION: Label extender sequence

<400> SEQUENCE: 45
gataacgaac gagactctgg cattttttga agttaccgtt tt          42

<210> SEQ ID NO 46
<211> LENGTH: 42
<212> TYPE: DNA
<213> ORGANISM: Artificial Sequence
<220> FEATURE:
<223> OTHER INFORMATION: Label extender sequence

<400> SEQUENCE: 46
gagcgatttg tctggttaat tccttttttct gagtcaaagc at          42

<210> SEQ ID NO 47
<211> LENGTH: 38
<212> TYPE: DNA
<213> ORGANISM: Artificial Sequence
<220> FEATURE:
<223> OTHER INFORMATION: Label extender sequence

<400> SEQUENCE: 47
gattccgtgg gtggtggtgt ttttgaagtt accgtttt          38

<210> SEQ ID NO 48
<211> LENGTH: 45
<212> TYPE: DNA
<213> ORGANISM: Artificial Sequence
<220> FEATURE:
<223> OTHER INFORMATION: Label extender sequence

<400> SEQUENCE: 48
gattgacaga ttgatagctc tttctctttt tctgagtcaa agcat          45

```
<210> SEQ ID NO 49
<211> LENGTH: 39
<212> TYPE: DNA
<213> ORGANISM: Artificial Sequence
<220> FEATURE:
<223> OTHER INFORMATION: Label extender sequence

<400> SEQUENCE: 49
caacacggga aacctcaccc tttttgaagt taccgtttt                               39

<210> SEQ ID NO 50
<211> LENGTH: 39
<212> TYPE: DNA
<213> ORGANISM: Artificial Sequence
<220> FEATURE:
<223> OTHER INFORMATION: Label extender sequence

<400> SEQUENCE: 50
gcctgcggct taatttgact tttttctgag tcaaagcat                               39

<210> SEQ ID NO 51
<211> LENGTH: 39
<212> TYPE: DNA
<213> ORGANISM: Artificial Sequence
<220> FEATURE:
<223> OTHER INFORMATION: Label extender sequence

<400> SEQUENCE: 51
ggggagtatg gttgcaaagc tttttgaagt taccgtttt                               39

<210> SEQ ID NO 52
<211> LENGTH: 39
<212> TYPE: DNA
<213> ORGANISM: Artificial Sequence
<220> FEATURE:
<223> OTHER INFORMATION: Label extender sequence

<400> SEQUENCE: 52
ccaaagtctt tgggttccgg tttttctgag tcaaagcat                               39

<210> SEQ ID NO 53
<211> LENGTH: 39
<212> TYPE: DNA
<213> ORGANISM: Artificial Sequence
<220> FEATURE:
<223> OTHER INFORMATION: Label extender sequence

<400> SEQUENCE: 53
gaccataaac gatgccgacc tttttgaagt taccgtttt                               39

<210> SEQ ID NO 54
<211> LENGTH: 42
<212> TYPE: DNA
<213> ORGANISM: Artificial Sequence
<220> FEATURE:
<223> OTHER INFORMATION: Label extender sequence

<400> SEQUENCE: 54
cgatcagata ccgtcgtagt tcctttttct gagtcaaagc at                           42

<210> SEQ ID NO 55
<211> LENGTH: 45
<212> TYPE: DNA
<213> ORGANISM: Artificial Sequence
<220> FEATURE:
<223> OTHER INFORMATION: Label extender sequence

<400> SEQUENCE: 55
```

```
ccaagaatgt tttcattaat caagaatttt tgaagttacc gtttt          45
```

<210> SEQ ID NO 56
<211> LENGTH: 40
<212> TYPE: DNA
<213> ORGANISM: Artificial Sequence
<220> FEATURE:
<223> OTHER INFORMATION: Label extender sequence

<400> SEQUENCE: 56

```
ggaccagagc gaaagcattt gttttctga gtcaaagcat               40
```

<210> SEQ ID NO 57
<211> LENGTH: 43
<212> TYPE: DNA
<213> ORGANISM: Artificial Sequence
<220> FEATURE:
<223> OTHER INFORMATION: Label extender sequence

<400> SEQUENCE: 57

```
catctgtggg attatgactg aacgtttttg aagttaccgt ttt           43
```

<210> SEQ ID NO 58
<211> LENGTH: 38
<212> TYPE: DNA
<213> ORGANISM: Artificial Sequence
<220> FEATURE:
<223> OTHER INFORMATION: Label extender sequence

<400> SEQUENCE: 58

```
gccaatgggg cgaagctact ttttctgagt caaagcat                 38
```

<210> SEQ ID NO 59
<211> LENGTH: 40
<212> TYPE: DNA
<213> ORGANISM: Artificial Sequence
<220> FEATURE:
<223> OTHER INFORMATION: Label extender sequence

<400> SEQUENCE: 59

```
gaaccgcagg ttcagacatt tttttgaag ttaccgtttt                40
```

<210> SEQ ID NO 60
<211> LENGTH: 43
<212> TYPE: DNA
<213> ORGANISM: Artificial Sequence
<220> FEATURE:
<223> OTHER INFORMATION: Label extender sequence

<400> SEQUENCE: 60

```
tggtaatcct gctcagtacg agagtttttc tgagtcaaag cat           43
```

<210> SEQ ID NO 61
<211> LENGTH: 43
<212> TYPE: DNA
<213> ORGANISM: Artificial Sequence
<220> FEATURE:
<223> OTHER INFORMATION: Label extender sequence

<400> SEQUENCE: 61

```
cctactgatg atgtgttgtt gccattttg aagttaccgt ttt            43
```

<210> SEQ ID NO 62
<211> LENGTH: 44
<212> TYPE: DNA
<213> ORGANISM: Artificial Sequence
<220> FEATURE:
<223> OTHER INFORMATION: Label extender sequence

<400> SEQUENCE: 62
ccgtcgtgag acaggttagt tttactttttt ctgagtcaaa gcat        44

<210> SEQ ID NO 63
<211> LENGTH: 44
<212> TYPE: DNA
<213> ORGANISM: Artificial Sequence
<220> FEATURE:
<223> OTHER INFORMATION: Label extender sequence

<400> SEQUENCE: 63
cgttggattg ttcacccact aatagttttt gaagttaccg tttt        44

<210> SEQ ID NO 64
<211> LENGTH: 40
<212> TYPE: DNA
<213> ORGANISM: Artificial Sequence
<220> FEATURE:
<223> OTHER INFORMATION: Label extender sequence

<400> SEQUENCE: 64
tgtgaagcag aattcgccaa gttttttctga gtcaaagcat        40

<210> SEQ ID NO 65
<211> LENGTH: 43
<212> TYPE: DNA
<213> ORGANISM: Artificial Sequence
<220> FEATURE:
<223> OTHER INFORMATION: Label extender sequence

<400> SEQUENCE: 65
tttcagtacg aatacagacc gtgattttg aagttaccgt ttt        43

<210> SEQ ID NO 66
<211> LENGTH: 41
<212> TYPE: DNA
<213> ORGANISM: Artificial Sequence
<220> FEATURE:
<223> OTHER INFORMATION: Label extender sequence

<400> SEQUENCE: 66
caaaagctcg cttgatcttg attttttctg agtcaaagca t        41

<210> SEQ ID NO 67
<211> LENGTH: 40
<212> TYPE: DNA
<213> ORGANISM: Artificial Sequence
<220> FEATURE:
<223> OTHER INFORMATION: Label extender sequence

<400> SEQUENCE: 67
agctcaggga ggacagaaac cttttttgaag ttaccgtttt        40

<210> SEQ ID NO 68
<211> LENGTH: 37
<212> TYPE: DNA
<213> ORGANISM: Artificial Sequence
<220> FEATURE:
<223> OTHER INFORMATION: Label extender sequence

<400> SEQUENCE: 68
cgcaggtgtc ctaaggcgtt tttctgagtc aaagcat        37

```
<210> SEQ ID NO 69
<211> LENGTH: 14
<212> TYPE: DNA
<213> ORGANISM: Artificial Sequence
<220> FEATURE:
<223> OTHER INFORMATION: Blocking label sequence

<400> SEQUENCE: 69
ggcgcccgcc acca                                                           14

<210> SEQ ID NO 70
<211> LENGTH: 20
<212> TYPE: DNA
<213> ORGANISM: Artificial Sequence
<220> FEATURE:
<223> OTHER INFORMATION: Blocking label sequence

<400> SEQUENCE: 70
gctcactgca acctccacct                                                     20

<210> SEQ ID NO 71
<211> LENGTH: 22
<212> TYPE: DNA
<213> ORGANISM: Artificial Sequence
<220> FEATURE:
<223> OTHER INFORMATION: Blocking label sequence

<400> SEQUENCE: 71
ggagtgcagt ggcatgatct tg                                                  22

<210> SEQ ID NO 72
<211> LENGTH: 19
<212> TYPE: DNA
<213> ORGANISM: Artificial Sequence
<220> FEATURE:
<223> OTHER INFORMATION: Blocking label sequence

<400> SEQUENCE: 72
gggcaccacc aggagtgga                                                      19

<210> SEQ ID NO 73
<211> LENGTH: 14
<212> TYPE: DNA
<213> ORGANISM: Artificial Sequence
<220> FEATURE:
<223> OTHER INFORMATION: Blocking label sequence

<400> SEQUENCE: 73
ggcgatgcgg cggc                                                           14

<210> SEQ ID NO 74
<211> LENGTH: 22
<212> TYPE: DNA
<213> ORGANISM: Artificial Sequence
<220> FEATURE:
<223> OTHER INFORMATION: Blocking label sequence

<400> SEQUENCE: 74
cgatgtcggc tcttcctatc at                                                  22

<210> SEQ ID NO 75
<211> LENGTH: 22
<212> TYPE: DNA
<213> ORGANISM: Artificial Sequence
<220> FEATURE:
<223> OTHER INFORMATION: Blocking label sequence

<400> SEQUENCE: 75
```

-continued

```
ccacagggat aactggcttg tg                                          22

<210> SEQ ID NO 76
<211> LENGTH: 24
<212> TYPE: DNA
<213> ORGANISM: Artificial Sequence
<220> FEATURE:
<223> OTHER INFORMATION: Blocking label sequence

<400> SEQUENCE: 76
aagcaggagg tgtcagaaaa gtta                                        24

<210> SEQ ID NO 77
<211> LENGTH: 16
<212> TYPE: DNA
<213> ORGANISM: Artificial Sequence
<220> FEATURE:
<223> OTHER INFORMATION: Blocking label sequence

<400> SEQUENCE: 77
aagcggggcc tcacga                                                 16

<210> SEQ ID NO 78
<211> LENGTH: 38
<212> TYPE: DNA
<213> ORGANISM: Mus sp.

<400> SEQUENCE: 78
tgcctcccga gtgctggttt ttctcttgga aagaaagt                         38

<210> SEQ ID NO 79
<211> LENGTH: 41
<212> TYPE: DNA
<213> ORGANISM: Mus sp.

<400> SEQUENCE: 79
ctcagaaatc cgcctgcctc tttttctctt ggaaagaaag t                     41

<210> SEQ ID NO 80
<211> LENGTH: 40
<212> TYPE: DNA
<213> ORGANISM: Mus sp.

<400> SEQUENCE: 80
agaccaggct ggcctcgaat ttttctcttg gaaagaaagt                       40

<210> SEQ ID NO 81
<211> LENGTH: 43
<212> TYPE: DNA
<213> ORGANISM: Mus sp.

<400> SEQUENCE: 81
agacagggtt tctctgtagc ccttttttctc ttggaaagaa agt                  43

<210> SEQ ID NO 82
<211> LENGTH: 48
<212> TYPE: DNA
<213> ORGANISM: Mus sp.

<400> SEQUENCE: 82
gattaaaggc atgcaccacc atttttctga gtcaaagcat gaagttac              48

<210> SEQ ID NO 83
<211> LENGTH: 50
```

```
<212> TYPE: DNA
<213> ORGANISM: Mus sp.

<400> SEQUENCE: 83
tggtgtcctg gaactcactc tgatttttct gagtcaaagc atgaagttac          50

<210> SEQ ID NO 84
<211> LENGTH: 129
<212> TYPE: DNA
<213> ORGANISM: Mus sp.

<400> SEQUENCE: 84
ccgggcatgg tggtgcatgc ctttaatccc agcactcggg aggcagaggc aggcggattt    60
ctgagttcga ggccagcctg gtcttcagag tgagttccag gacaccaggg ctacagagaa   120
accctgtct                                                           129
```

METHOD FOR PREDICTING THE LEVEL OF DAMAGE TO CELLS BY MEASURING FREE CIRCULATING ALU NUCLEIC ACID

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DIAC00101USSeqList_ST25.txt, date recorded: May 13, 2009, file size 18 kilobytes).

FIELD OF THE INVENTION

This invention relates generally to detecting and/or measuring DNA markers related to cell damage, e.g., as a consequence of pathophysiological or traumatic insults, especially in a nuclear accident, bioterror attack, tumorigenesis, infections or in individuals with cardiovascular disease(s). In particular, this invention relates to using one or more generic biomarkers to detect and/or measure cell damages in a subject.

BACKGROUND OF THE INVENTION

Genomic DNA in healthy cells is normally confined within the nucleus of the cells. However, genomic DNA is released into the circulation during cell aging where cells undergo programmed cell death or apoptosis, or during early disease states. These circulating DNAs are often not detectable in healthy individuals because of the homeostatic ability to efficiently eliminate them from the circulation. Likewise, circulating DNA in individuals during early disease stage, such as during early tumorigenesis, do not express tumor specific markers in amounts high enough for early detection using currently available nucleic acid detection methods. Although circulating DNA from individuals in the early stage of tumor development may be higher than normal healthy individuals, there are currently no biomarkers that would discriminate between circulating DNA released as a result of tumorigenesis and normal cell aging in individuals. In addition, most if not all of the free circulating DNA is eliminated from the circulation using the same cell machinery as in healthy individuals.

Furthermore, in circumstances where individuals have been exposed to high levels of radiation, for example in a nuclear accident, or high levels of radiation and/or infectious agent in a bioterror attack, massive cell damage ensues resulting in high levels of genomic DNA being released into circulation. However, there is not currently available a method for an efficient, reliable and inexpensive means for detecting these individuals for the purpose of treating and quarantining these individuals from cross-contaminating individuals who have not been exposed to such agents.

Accordingly, there is a need in the art for methods and/or biomarkers useful for detecting and/or measuring the state or condition of a subject, especially based on genomic DNA released into circulation upon pathophysiological insults.

SUMMARY OF THE INVENTION

The present invention is based, in part, on the discovery that certain nucleotides, e.g., genomic DNA in free circulation of a subject can be used as a biomarker to indicate the state of the subject, e.g., subject's exposure to any pathophysiological insult. Accordingly, the present invention provides methods, kits, and related biomarkers and reagents useful for detecting cell damage associated with a physiopathologica insult.

In one aspect of the invention, it provides a method for detecting cell damage related to a pathophysiological insult in a subject. The method includes detecting the presence or absence of a free circulating generic biomarker in a biological sample of the subject, wherein the presence of the free circulating generic biomarker is indicative of cell damage related to a pathophysiological insult in the subject.

The pathophysiological insults can be a physical insult including without any limitation exposure to high levels of irradiation, for example, in a nuclear accident or a bomb attack. In one embodiment, the pathophysiological insult can be due to infectious agents, such as but not limited to infections by viruses, bacteria, and or parasite, either naturally or as a result of bioterrorism. In another embodiment, the pathophysiological insult can be due to the development and progression of a disease state, such as in tumorigenesis, heart, liver, lung or kidney disease. In yet another embodiment, the pathophysiological insult can be a chemical insult such as chemotherapy and other hematotoxic agents, carbon tetrachloride and other hepatotoxic agents, oxidizing agents and acids and other topically or ingested necrotizing agents. In another embodiment, the pathophysiological insult can be a traumatic physical insult such as in head injuries or burns resulting from accidents.

The free circulating generic biomarker of the present invention comprises nucleotides that are present as free circulating nucleotides or free plasma nucleotides in a subject and are not associated or located within any cell. Examples of generic biomarkers include sequences selected from those having Alu sequence, or sequences derived from telomeres, and genes encoding 18S/28S ribosomal RNA.

In another aspect, the present invention provides a method for detecting cell damage resulting from a pathophysiological insult comprising determining the level of a free circulating generic biomarker in a biological sample of a subject. In one embodiment, the level of the free circulating generic biomarker relates to a physical insult such as but not limited to exposure to radiation, for example, in a nuclear accident or a dirty bomb attack.

In another embodiment, the level of the free circulating generic biomarker relates to a pathophysiological insult due to infectious agents such as but not limited to infections by viruses, bacteria, and or parasite, either naturally or as a result of bioterrorism. In another embodiment the level of the free circulating generic biomarker relates to a pathophysiological insult as a result of the development and progression of a disease state, such as in tumorigenesis, heart, liver, lung or kidney disease.

In yet another embodiment, the level of the free circulating generic biomarker relates to a pathophysiological insult resulting from chemical exposure such as but not limited to an exposures to aerosols from chemical fires and industrial toxin exposure In another embodiment, the level of the free circulating generic biomarker relates to a pathophysiological insult due to a traumatic physical insult such as physical injuries, e.g., head injuries resulting from accidents, sports-related injuries and excessive exercise.

The present invention also provides a kit for detecting circulating nucleotides, e.g., DNAs due to damage to cells as a result of pathophysiological insults in individuals. In one embodiment, the kit comprises a probe set used for detecting free circulating nucleotides. In one embodiment the probe set comprises sequences that hybridize to the generic biomarkers that are present in the free circulating nucleotides or free plasma nucleotides in a biological samples, such as plasma or other body fluids. Examples of generic biomarkers include sequences selected from those having Alu sequence, sequences derived from telomeres, 18S/28S ribosomal RNA and other genomic DNA sequences.

In another embodiment, the probe set comprises a capture extender having sequences that hybridize to the generic biomarkers such as but not limited to Alu sequences, telomere sequences or 18S/28S ribosomal RNA sequences present in the free circulating nucleotides or free plasma nucleotides present in a biological sample obtained from a subject. In yet another embodiment, the probe set further comprises a label extender having sequences that hybridize to the generic biomarkers such as but not limited to Alu sequences, telomere sequences or 18S/28S ribosomal RNA sequences that are present in the free circulating nucleotides or free plasma nucleotides present in a biological sample obtained from a subject.

DETAILED DESCRIPTION OF THE INVENTION

Figure 1:
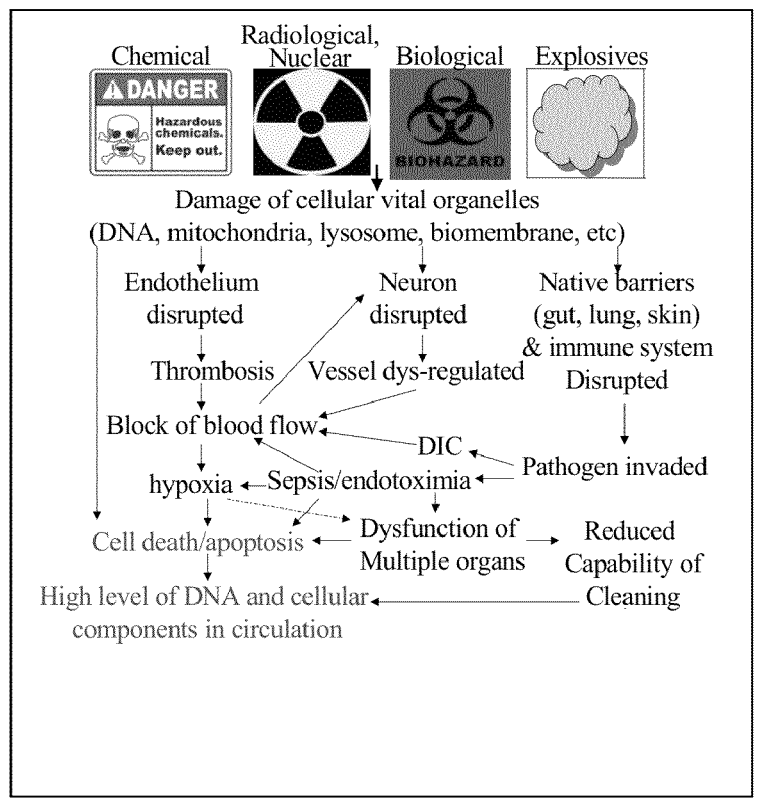
FIG. 1 shows the schematic where DNA is released into the circulation following insults from various pathophysiological processes.

The present invention is based, in part, on the discovery that certain nucleotides, e.g., genomic DNA in free circulation of a subject can be used as a biomarker to indicate the state of the subject, e.g., subject's exposure to any pathophysiological insult. Accordingly, the present invention provides methods, kits, and related biomarkers and reagents used for detecting cell damage associated with a pathophysiological insult.

In one aspect of the invention, it provides methods for detecting cell damage as a result of or associated with pathophysiological insults in individuals via detecting the presence or absence of one or more free circulating generic biomarkers in a biological sample obtained from a subject of interest.

The free circulating generic biomarker of the present invention can be any generic biomarker, e.g., DNA or RNA marker that is released into vascular system, present in circulation, e.g. blood or plasma, present in body fluid, e.g., plasma, serum, urine, or pleural effusion or is extracellular, e.g., outside of (not associated or located within) any cell, bound or unbound to the cell surface. The free circulating nucleotides, e.g., containing generic biomarker(s), as used herein can be used interchangeably with the term "cell free nucleotide", "cell free circulating nucleotide" or "free circulating nucleotide", "plasma nucleotide" or "cell free plasma nucleotide". According to the present invention, free circulating nucleotides, e.g., containing generic biomarkers can be obtained from a biological sample such as but not limited to blood sample, serum sample, plasma sample, urine sample, or a pleural effusion sample or a combination thereof.

The term "generic biomarkers" as used in the present invention are nucleotides (DNA or RNA) or other biological entities that function as markers associated with cellular release of genetic contents. In general, generic biomarkers are nucleotides, e.g., biomarkers present extracellularly, and optionally whose sequences per se or expressions or activities within cells and/or on cell surfaces does not constitute any significant part of a biomarker, e.g., are not specifically associated with any particular disease or condition. In particular, generic biomarkers of the present invention relies primarily on their extracellularly presence or activity to function as a biomarker.

In one embodiment, generic biomarkers are markers associated with cell death or cellular release of e.g., genetic contents such as DNA as a result of neoplasia such as cancer. In another embodiment, generic biomarkers are markers associated with cell death or cellular release of, e.g., genetic contents such as DNA as a result of exogenous insult, treatment, or traumatic impact to a subject, e.g., pathogen attack, damaging exposure, physical trauma, etc. In yet another embodiment, generic biomarkers are markers associated with cell death or cellular release of, e.g., genetic content such as DNA as a result of internal trauma or insult in a subject, e.g. cardiac infarction, autoimmune diseases, etc. In still another embodiment, generic biomarkers are markers associated with cell death or cellular release of, e.g., genetic content such as DNA as a result of a pathophysiological insult, but not normal physiological process in a subject, e.g., aging.

In still yet another embodiment, generic biomarkers are repetitive sequences or elements, e.g., tandem repeats, etc., house keeping genes or elements, or any other sequences that are present in certain abundance in mammalian, e.g., human genomes. For instance, generic biomarkers can be repetitive sequences or any sequence element that constitutes at least 1%, 2%, 3%, 4%, 5%, 6%, 7%, 8%, 9%, or 10% of the human genome.

In one exemplary embodiment, the generic biomarkers are markers having partial or whole Alu sequences. The Alu sequence is a short stretch of DNA originally characterized by the action of Alu restriction endonuclease, which recognizes the sequence 5' AG/CT 3'. The Alu sequence belongs to a family of repetitive elements present in mammalian genome such as the human genome. There are roughly over 300,000 Alu family members in the haploid genome. The Alu sequences are about 300 base pair long and there are over one million of these sequences interspersed throughout the human genome. It is estimated that about 10% of the human genome consists of Alu sequences.

Any Alu sequence, partial or whole can be used as generic biomarkers. In one embodiment, Alu sequences that are most abundant or have substantial abundance in the human genome are used as generic biomarkers. In another embodiment, Alu sequences that are uniquely associated with stress or insults to a subject are used as generic biomarkers.

Examples of Alu sequences that can be used as generic biomarkers include but are not limited to the sequences represented in SEQ ID NOS: 1 or 2 or fragments thereof. In one embodiment, generic biomarkers of the present invention are about 50%, 55%, 60%, 65%, 70%, 75%, 80%, 85%, 90%, 95%, 96%, 97%, 98%, 99% identical to SEQ ID NOS: 1 or 2.

In a further embodiment, the Alu sequence biomarkers can be detected using a probe set designed based on Alu sequences used as markers, e.g., according to QuantiGene™ methods. In general, a probe set includes a Capture Extender (CE), e.g., at least two, three, four, or five CEs, each containing one of sequences of SEQ ID NOS: 7-19 (See, Tables 1-3 below), a Label Extender (LE), e.g., at least one, two, three, four, or five LEs, each containing one of sequences of SEQ ID NOS: 32-44 (See, Table 6-8 below) and optionally a Blocking Label (BL), e.g., at least one, two, or three BLs each containing one of sequences of SEQ ID NOS: 69-71 (See, Table 11 below).

The length of CE, LE and BL can be from about 10 nucleotides to about 20 nucleotides in length, from about 20 nucleotide to about 30 nucleotides in length, or from about 30 nucleotides to 50 nucleotides in length. In one embodiment, the probe set includes CEs each containing one of sequences of SEQ ID NOS: 7-11, LEs each containing one of sequences of SEQ ID NOS: 32-35 and optionally a BL containing a sequence of SEQ ID NO: 69. In another embodiment, the probe set includes CEs each containing one of sequences of SEQ ID NOS: 12-15, LEs each containing one of sequences of SEQ ID NOS: 36-38. In yet another embodiment, the probe set includes CEs each containing one of sequences of SEQ ID NOS: 16-19, LEs each containing one of sequences of SEQ ID NOS: 39-44 and optionally BLs each containing one of sequences of SEQ ID NOS: 70 and 71.

In another exemplary embodiment, the generic biomarkers are markers having partial or whole sequences derived from genes encoding 18S/28S ribosomal RNA. Ribosomal RNA genes are organized in tandem repeats in mammalian genomes. In humans, there are about 300-400 such repeats organized in five clusters. Examples of 18S and 28S sequences that can be used as generic biomarkers include but are not limited to those represented in SEQ ID NOS: 3 or 4 or fragments thereof. In one embodiment, generic biomarkers of the present invention are about 50%, 55%, 60%, 65%, 70%, 75%, 80%, 85%, 90%, 95%, 96%, 97%, 98%, 99% identical to SEQ ID NOS: 3 or 4.

In a further embodiment, the 18S/28S rRNA sequence biomarkers can be detected using a probe set designed based on 18S/28S rRNA sequences used as markers, e.g., according to QuantiGene™ methods. In general, a probe set includes a Capture Extender (CE), e.g., at least two, three, four, or five CEs each containing one of sequences of SEQ ID NOS: 20-31 (See, Tables 4 and 5 below), a Label Extender (LE), e.g., at least one, two, three, four, or five LEs each containing one of sequences of SEQ ID NOS: 45-68 (See, Tables 9 and 10 below) and optionally a Blocking Label (BL), e.g., at least one, two, three, four, or five BLs each containing one of sequences of SEQ ID NOS: 72-77 (See, Table 11 below).

The length of CE LE and BL can be from about 10 nucleotide to about 20 nucleotide in length, from about 20 nucleotide to about 30 nucleotide in length, or from about 30 nucleotide to 50 nucleotide in length.

In a further embodiment, the generic biomarkers are markers having partial or whole sequences derived from telomeres. Telomere is involved in the replication and stability of the chromosome. It includes a region of repetitive DNA sequences of about six nucleotide bases at the end of the chromosome. The telomeric sequences can vary between approximately 300 to approximately 600 bp in length in yeast to many kilobases in humans. The sequences typically comprise an array of about 6 to about 8 bp of G-rich repeats, or less, such as TTAGGG, TTGGG, TTTTGGGG, etc. Examples of sequences useful for being used as generic biomarkers include but are not limited to SEQ ID NOS: 5 and 6 and fragments thereof. In one embodiment, generic biomarkers of the present invention are about 50%, 55%, 60%, 65%, 70%, 75%, 80%, 85%, 90%, 95%, 96%, 97%, 98%, or 99% identical to SEQ ID NOS: 5 or 6.

In a further embodiment, the telomeric sequence biomarkers can be detected using a probe set designed based on telomeric sequences used as markers, e.g., according to QuantiGene™ methods. In general, a probe set includes a Capture Extender (CE), e.g., at least two, three, four, or five CEs, a Label Extender (LE) e.g., at least one, two, three, four, or five LEs, and optionally a Blocking Label (BL), e.g., at least one, two, three, four, or five BLs. The length of CE, LE and BL can be from about 10 nucleotide to about 20 nucleotide in length, from about 20 nucleotide to about 30 nucleotide in length, or from about 30 nucleotide to 50 nucleotide in length.

The term "pathophysiological insult" as used herein means any physical or pathological impact or trauma, e.g., associated with an exogenous or internal event or source. In one embodiment, the pathophysiological insult is associated with an exogenous stress, impact or treatment to a subject. For example, it can be an instance of pathogen infection, exposure to hazardous material, physical injury, or any external event that is traumatic to a subject's system. In another embodiment, the pathophysiological insult is associated with an internal stress, impact or pathological event to a subject. For example, it can be any pathological event associated with cell death or programmed cell death, necrosis, cellular degradation, etc.

In one exemplary embodiment, the pathophysiological insult is an exposure to radiation or any other material or energy source that causes DNA damage. In one embodiment, the pathophysiological insult is an exposure to radiation in association with a nuclear incident, attack of nuclear weapon, etc.

In another embodiment, the pathophysiological insult is a chemical insult such as but not limited to caustic aerosols from industrial accidents or explosions, such as halogenated hydrocarbons or acids. Evaluating the severity of exposure to chemical weapon detonation is another example.

In another exemplary embodiment, the pathophysiological insult is due to infectious agents, such as but not limited to infections by viruses, bacteria, and or parasite, either by natural exposure to an infectious agent or as a result of bioterrorism.

Examples of viral families that can result in pathophysiological damage in cells include: Paramyxoviridae (e.g., parainfluenza, mumps, measles); Orthomyxoviridae (e.g., influenza); Hepdnaviridae (e.g., hepatitis); Adenoviridae (e.g., acute respiratory disease); Poxviridae (e.g., small pox); Herpesviridae (e.g., herpes, Karposi sarcoma); Papillomaviridae (e.g., HPV); Polyomaviridae (e.g., cystitis or mild or acute respiratory diseases); Parvoviridae; Rhabdoviridae (e.g., rabies); Filoviridae (e.g., hemorrhagic fever caused by Ebola virus and Marburg virus); Bunyaviridae (e.g., encephalitis, Hantavirus respiratory syndrome, Rift Valley fever); Arenaviridae (e.g., aseptic meningitis, encephalitis, meningoencephalitis, Lassa fever); Coronaviridae (e.g., severe acute respiratoroy syndrome or SARS); Flaviviradae (e.g., Dengue hemorrhagic fever); Togaviridae; Picornaviridae (e.g.,); Caliciviridae (e.g., winter vomiting disease); Astroviridae (e.g., gastroenteritis); Retroviridae (e.g., HIV, HTLV) and Reoviridae (e.g., Colorado Tick fever).

Non-limiting examples of bacteria that can cause pathophysiological damage in infected cells are: *B. pertussis; Leptospira Pomona; S. paratyphi* A and B; *C. diphtheriae, C. tetani, C. botulinum, C. perfringens, C. feseri* and other gas gangrene bacteria; *B. anthracis; P. pestis; P. multocida; Neisseria meningitides; N. gonorrheae; Hemophilus influenzae; Actinomyces* (e.g., Norcardia); Acinetobacter; Bacillaceae (e.g., *Bacillus anthrasis*); *Bacteroides* (e.g., *Bacteroides fragilis*); Blastomycosis; *Bordetella* (*Bordetella pertusi*); *Borrelia* (e.g., *Borrelia burgdorferi*); *Brucella; Campylobacter; Chlamydia; Coccidioides; Corynebacterium* (e.g., *Corynebacterium diptheriae*); *E. coli* (e.g., Enterotoxigenic *E. coli* and Enterohemorrhagic *E. coli*); *Enterobacter* (e.g. *Enterobacter aerogenes*); Enterobacteriaceae (*Klebsiella, Salmonella* (e.g., *Salmonella typhi, Salmonella enteritidis, Serratia, Yersinia, Shigella*); Erysipelothrix; *Haemophilus* (e.g., *Haemophilus influenza* type B); *Helicobacter; Legionella* (e.g., *Legionella pneumophila*); Leptospira; *Listeria* (e.g., *Listeria monocytogenes*); *Mycoplasma; Mycobacterium* (e.g., *Mycobacterium leprae, Mycobacterium tuberculosis* and *Mycobacterium bovis*); *Vibrio* (e.g., *Vibrio cholerae*); Pasteurellacea (*Pasteurella haemolytica*); *Proteus; Pseudomonas* (e.g., *Pseudomonas aeruginosa*); Rickettsiaceae; Spirochetes (e.g., *Treponema* spp., *Leptospira* spp., *Borrelia* spp.); *Shigella* spp.; *Meningiococcus; Pneumococcus* and *Streptococcus* (e.g., *Streptococcus pneumoniae* and Groups A, B, and C Streptococci); Ureaplasmas; *Treponema pollidum*; and *Staphylococcus* (*Staphylococcus aureus* and *Staphylococcus epidermidis*).

Non-limiting examples of parasites or protozoa which can cause pathophysiological damage in infected cells include: leishmaniasis (*Leishmania tropica mexicana, Leishmania tropica, Leishmania major, Leishmania aethiopica, Leishmania braziliensis, Leishmania donovani, Leishmania infantum, Leishmania chagasi*); trypanosomiasis (*Trypanosoma brucei gambiense, Trypanosoma brucei rhodesiense*); toxoplasmosis (*Toxoplasma gondii*); schistosomiasis (*Schistosoma haematobium, Schistosoma japonicum, Schistosoma mansoni, Schistosoma mekongi, Schistosoma intercalatum*); malaria (*Plasmodium virax, Plasmodium falciparium, Plasmodium malariae* and *Plasmodium ovate*); Amebiasis (*Entamoeba histolytica*); Babesiosis (Babesiosis microti); Cryptosporidiosis (*Cryptosporidium parvum*); Dientamoebiasis (*Dientamoeba fragilis*); Giardiasis (*Giardia lamblia*); Helminthiasis and *Trichomonas* (*Trichomonas vaginalis*). The above lists are meant to be illustrative and by no means are meant to limit the invention to those particular bacterial, viral or parasitic organisms.

In another embodiment, the pathophysiological insult can be due to the development and progression of a disease state, e.g., associated with cell death (programmed cell death), cell damage, necrosis, etc. In one embodiment, the pathophysiological insult is tumorigenesis or neoplasia in a subject. In another embodiment, the pathophysiological insult is substantial tumorigenesis or neoplasia at more than one location in a subject, for example, metastasis in lymph nodes etc. Examples of diseases resulting from tumorigenesis or neoplasia, include but not limited to leukemia, breast cancer, prostate cancer, liver cancer, stomach cancer, colon cancer, melanoma, lymphoma, lung cancer, pancreatic cancer, brain tumor, oral cancer etc.

In yet another embodiment, the pathophysiological insult is an autoimmune disease. Examples of autoimmune disease include vertiligo, scleroderma, rheumatoid arthritis, Chagas disease, diabetes mellitus type 1, Hashimoto disease, ankylosing spondylitis, Grave's disease, Guillain-Barre Syndrome, etc.

In yet another embodiment, the pathophysiological insult is a cardiovascular disease. Examples of cardiovascular disease include acute vascular obstruction, such as pulmonary embolism and cardiac infarction resulting in apoptosis of heart cells which in turn causes the release of cell free nucleotides, e.g., DNA into circulation. In yet another embodiment, the pathophysiological insult is hepatic disease, lung disease or kidney disease, etc., especially conditions associated with cell death and necrosis.

In still another embodiment, the pathophysiological insult is a traumatic physical insult such as head injuries resulting from accidents. In still another embodiment, the pathophysiological insult can be from sports injury, such as in boxing, football or strenuous exercise, etc.

According to the present invention, the method for detecting cell damage related to a pathophysiological insult in a subject can include qualitative and/or quantitative detection of the cell damage. In one embodiment, the method of the present invention includes detection of presence or absence of one or more free circulating generic biomarkers in a biological sample obtained from a subject, which is exposed to or suspected of being exposed to a pathophysiological insult. In another embodiment, the method of the present invention includes detection of the level of one or more free circulating generic biomarkers in a biological sample obtained from a subject to monitor the progression, the extent or level of, or the effect of the treatment for a pathophysiological insult.

The method of detection of the present invention can be carried out with or without amplification of the free circulating generic biomarker. In one embodiment, the method of detection can be, but not limited to real-time PCR, quantitative PCR, fluorescent PCR, RT-MSP (RT methylation specific polymerase chain reaction), PicoGreen™ (Molecular Probes, Eugene, Oreg.) detection of DNA, radioimmunoassay, direct radio-labeling of DNA, etc. In another embodiment, the method of detection of the present invention can be carried out without relying on amplification, e.g., without generating any copy or duplication of a target sequence, without involvement of any polymerase, or without the need for any thermal cycling. In yet another embodiment, the method of detection of the present invention is carried out using the principles set forth in the QuantiGene™ method described in U.S. application Ser. No. 11/471,025, filed Jun. 19, 2006, and is incorporated herein by reference.

The QuantiGene™ method uses a branched DNA technology in a series of hybridization reactions without the need for thermal cycling for amplification of a signal. In principle, it uses a set of primary probes to hybridize to a target sequence and the presence of such hybridization is intensified via additional probes hybridizing to part of these primary probes. In other words, the method intensifies the signal of hybridization by multiple layers of probe hybridization instead of any actual nucleotide sequence amplification.

Figure 3:
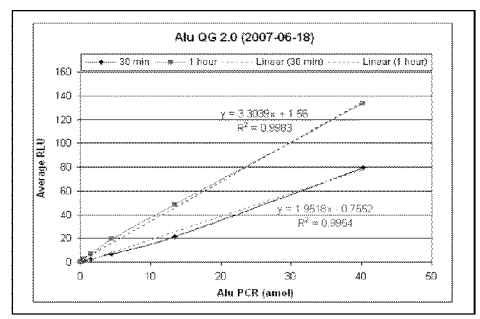
FIG. 3 shows the correlation of relative light units (RLU) emitted from streptavidin-conjugated phycoerythrin labeled probe bound to the generic marker, Alu sequences.
Figure 3:
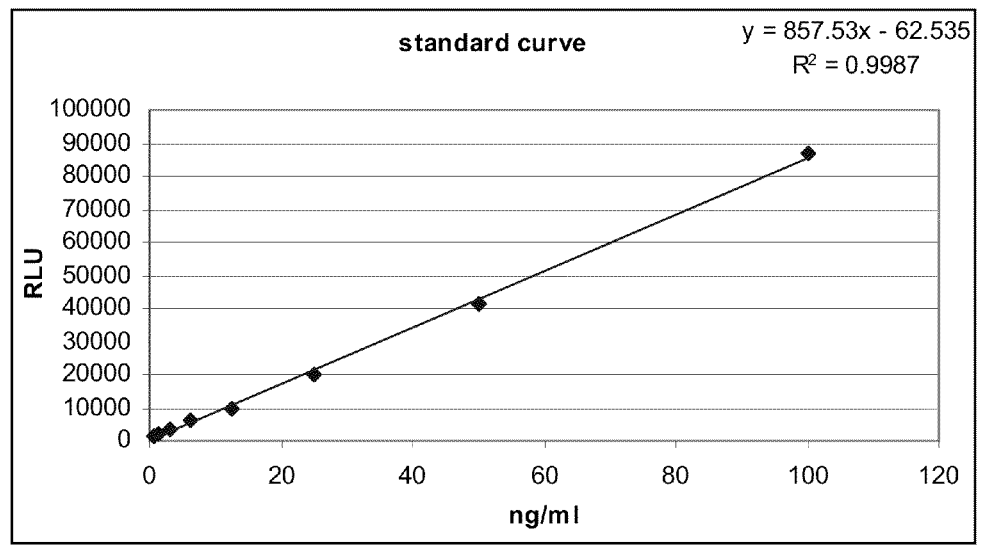

In one exemplary embodiment for the branched DNA technology, about 30 or more different oligonucleotide probes are used to bind specifically to a target DNA or RNA. Briefly, a nucleic acid such as free circulating DNA (linear or circular) is captured to a solid support by hybridizing to a set of probes, e.g., Capture Extenders (CEs), which in turn hybridizing to a set of probes, e.g., Capture Probes (CPs) attached to the solid support, e.g., beads, etc. Subsequently another set of probes, e.g., Label Extenders (LEs) can be used to further hybridize to the target nucleotide captured on the solid support. The signal of such hybridization can be intensified either by directly detecting the multiple hybridization of LEs to the target nucleotide on the solid support, or alternatively by further hybridization of one or more set of probes, e.g., pre-Amplifier probe, Amplifier probe, etc. to the hybridized LEs, or both. In one particular embodiment, the detection of such hybridization is carried out using a detectable entity conjugated with streptavidin while the corresponding probes are biotinylated. (See, FIG. 3)

In one embodiment, the probe set comprises the Capture Extender and the Label Extender having sequences that recognize and bind to Alu sequences. In another embodiment, the Capture Extender and the Label Extender are designed to recognize and bind to telomeric sequences. In another embodiment, Capture Extender and the Label Extender are designed to recognize and bind to 18S or 28 ribosomal RNA sequences.

In another aspect of the invention, the method for detecting cell damage resulting from a pathophysiological insult comprises determining the expression profile of a free circulating generic biomarker in a biological sample of a subject. In general, the expression profile of the free circulating generic biomarker of the present invention includes any parameter or data or qualitative or quantitative description associated with the presence or absence of the free circulating generic biomarker.

In one embodiment, the expression profile of the free circulating generic biomarker includes the level or concentration of one or more free circulating generic biomarkers. In another embodiment, the expression profile of the free circulating generic biomarker includes the presence or absence of a group or combination of free circulating generic biomarkers. In yet another embodiment, the expression profile of the free circulating generic biomarkers includes the level or concentration of one or more free circulating generic biomarkers in relation to a predetermined timeline or a timeline in association with the occurrence of a pathophysiological insult. In yet another embodiment, the expression profile of the free circulating generic biomarkers includes a combination of parameters, e.g., concentration, presence or absence with respect to a pre-determined timeline, extent of cell damage, the nuclear acid release kinetics, the balance between the gene production/fragmentation and the rate of body clearance, etc. In still another embodiment, the expression profile of the free circulating generic biomarkers includes one or more factors such as concentration, timeline, rate of increase, rate of resolution to baseline, peak level, differential expression of different generic markers, and time dependant changes in the differential expression of different generic markers.

According to another aspect of the present invention, it provides a kit for detecting free circulating generic biomarker due to cell damage as a result of pathophysiological insults in a subject. In one embodiment, the kit comprises a probe set useful for detecting free circulating generic biomarkers. In one embodiment the probe set comprises sequences that hybridize to the free circulating generic biomarkers.

In one exemplary embodiment, the probe set comprises a capture extender (CE) having sequences that hybridize to the generic biomarkers. In one embodiment, the probe set comprises a capture extender of probe set 1 derived from the Alu sequence of SEQ ID NO: 1. Examples of capture extenders derived from SEQ ID NO: 1 include SEQ ID NOS: 7, 8, 9, 10 and 11. (See, Table 1)

TABLE 1

Capture Extender of Probe Set 1 derived from the Alu sequence of SEQ ID NO: 1.

| SEQ ID NO: | CAPTURE EXTENDER NUCLEOTIDE SEQUENCE OF PROBE SET 1 |
|---|---|
| 7 | atttttagtagagacggggtttcaTTTTTctcttggaaagaaagt |
| 8 | cgcccggctaattttttgtTTTTTctcttggaaagaaagt |
| 9 | cgcctcccgggttcacgTTTTTctcttggaaagaaagt |
| 10 | ggagtgcagtggcgcgaTTTTTctcttggaaagaaagt |
| 11 | cgctctgtcgcccaggctTTTTTctcttggaaagaaagt |

In another embodiment, the probe set comprises a capture extender of probe set 2 derived from the Alu sequence of SEQ ID NO: 1. Examples of capture extender derived from SEQ ID NO: 1 include SEQ ID NOS: 12, 13, 14, 15 (See, Table 2).

TABLE 2

Capture Extender of Probe Set 2 derived from the Alu sequence of SEQ ID NO: 1

| SEQ ID NO: | CAPTURE EXTENDER NUCLEOTIDE SEQUENCE OF PROBE SET 2 |
|---|---|
| 12 | cgcccggctaattttttgtattttagtagagacTTTTTctcttggaaagaaagt |
| 13 | tctcctgcctcagcctcccgagtagctTTTTTctcttggaaagaaagt |
| 14 | cgcctcccgggttcacgccatTTTTTctcttggaaagaaagt |
| 15 | gtcgcccaggctggagtgcagtggTTTTTctcttggaaagaaagt |

In another embodiment, the probe set comprises a capture extender derived from the Alu sequence of SEQ ID NO: 2. Examples of capture extender derived from SEQ ID NO: 2 include SEQ ID NOS: 16, 17, 18 and 19. (See, Table 3).

TABLE 3

Capture Extender of Probe Set derived from the Alu sequence of SEQ ID NO: 2.

| SEQ ID NO: | CAPTURE EXTENDER NUCLEOTIDE SEQUENCE OF ALU SEQ ID NO: 2 |
|---|---|
| 16 | caaagtgctgggattacaggcTTTTTctcttggaaagaaagt |
| 17 | tttcattatattggtcaggctggtTTTTTctcttggaaagaaagt |
| 18 | gctgggattacaggcacccTTTTTctcttggaaagaaagt |
| 19 | cgctctgtcgcccaggctTTTTTctcttggaaagaaagt |

In another embodiment, the probe set comprises a capture extender, which is designed based on the 18S sequence of SEQ ID NO: 3. Examples of capture extenders based on 18S SEQ ID NO: 3 include SEQ ID NOS: 20, 21, 22, 23, 24 and 25. (See, Table 4)

TABLE 4

Capture Extender of Probe Set derived from the 18S sequence of SEQ ID NO: 3.

| SEQ ID NO: | CAPTURE EXTENDER NUCLEOTIDE SEQUENCE OF 18S |
|---|---|
| 20 | catggccgttcttagttggtgTTTTTctcttggaaagaaagt |
| 21 | ggcccggacacggacagTTTTTctcttggaaagaaagt |
| 22 | tgaaacttaaaggaattgacggaaTTTTTctcttggaaagaaagt |
| 23 | gggcagcttccgggaaaTTTTTctcttggaaagaaagt |
| 24 | gttattcccatgacccgccTTTTTctcttggaaagaaagt |
| 25 | cgaaagtcggaggttcgaagaTTTTTctcttggaaagaaagt |

In another embodiment the probe set comprises a capture extender which is designed based on the 28S sequence of SEQ ID NO: 4. Examples of capture extenders based on 18S SEQ ID NO: 4 include SEQ ID NOS: 26, 27, 28, 29, 30 and 31. (See, Table 5)

TABLE 5

Capture Extender of Probe Set derived from the 28S sequence of SEQ ID NO: 4.

| SEQ ID NO: | CAPTURE EXTENDER NUCLEOTIDE SEQUENCE OF 28S |
|---|---|
| 26 | ggtgtatgtgcttggctgaggaTTTTTctcttggaaagaaagt |
| 27 | ggaacgtgagctgggtttagaTTTTTctcttggaaagaaagt |
| 28 | cgacgtcgcttttgatccttTTTTTctcttggaaagaaagt |
| 29 | gcggccaagcgttcatagTTTTTctcttggaaagaaagt |
| 30 | tccttctgaccttttgggttttTTTTTctcttggaaagaaagt |
| 31 | tcccgtggagcagaagggTTTTTctcttggaaagaaagt |

In another embodiment, the probe set further comprises a label extender having sequences that hybridize to the generic biomarkers. In one embodiment, the probe set comprises a label extender of probe set 1 derived from the Alu sequence of SEQ ID NO: 1. Examples of label extenders derived from SEQ ID NO: 1 include SEQ ID NOS: 32, 33, 35 and 35. (See, Table 6).

TABLE 6

Label Extender of Probe Set 1 derived from the Alu sequence of SEQ ID NO: 1.

| SEQ ID NO: | LABEL EXTENDER NUCLEOTIDE SEQUENCE OF PROBE SET 1 |
|---|---|
| 32 | ccgtgttagccaggatggtctTTTTTctgagtcaaagcatgaagttac |
| 33 | tcccgagtagctgggactacaTTTTTctgagtcaaagcatgaagttac |
| 34 | ccattctcctgcctcagccTTTTTctgagtcaaagcatgaagttac |
| 35 | tctcggctcactgcaagctcTTTTTctgagtcaaagcatgaagttac |

In another embodiment the probe set comprises a label extender of probe set 2 derived from the Alu sequence of SEQ ID NO: 1. Examples of label extender of probe set 2 derived from SEQ ID NO: 1 include SEQ ID NOS: 36, 37, and 38. (See, Table 7)

TABLE 7

Label Extender of Probe Set 2 derived from the Alu sequence of SEQ ID NO: 1.

| SEQ ID NO: | LABEL EXTENDER NUCLEOTIDE SEQUENCE OF PROBE SET 2 |
|---|---|
| 36 | ggggtttcaccgtgttagccaggatggtctTTTTTctgagtcaaagcatgaagttac |
| 37 | gggactacaggcgcccgccaccaTTTTTctgagtcaaagcatgaagttac |
| 38 | cgcgatctcggctcactgcaagctcTTTTTctgagtcaaagcatgaagttac |

In another embodiment, the probe set comprises a label extender derived from the Alu sequence of SEQ ID NO: 2. Examples of label extender derived from SEQ ID NO: 2 include SEQ ID NOS: 39, 40, 41, 42, 43 and 44. (See, Table 8).

TABLE 8

Label Extender of Probe Set 2 derived from the Alu sequence of SEQ ID NO: 2.

| SEQ ID NO: | LABEL EXTENDER NUCLEOTIDE SEQUENCE OF SEQ ID NO: 2 |
|---|---|
| 39 | ccaccagcttcggcctccTTTTTctgagtcaaagcatgaagttac |
| 40 | ctcaaactcctgacctcaagtgatTTTTTctgagtcaaagcatgaagttac |
| 41 | tttttgtattttagtagagatggggTTTTTctgagtcaaagcatgaagttac |
| 42 | gccaccacgcccagctaaTTTTTctgagtcaaagcatgaagttac |
| 43 | ctgcctcagcctcccaagtaTTTTTctgagtcaaagcatgaagttac |
| 44 | cccaggttcaagcgattctcTTTTTctgagtcaaagcatgaagttac |

In another embodiment, the probe set comprises a label extender, which is designed based on the 18S sequence of SEQ ID NO: 3. Examples of label extenders based on 18S SEQ ID NO: 3 include SEQ ID NOS: 45, 46, 47, 48, 49, 50, 51, 52, 53, 54, 55 and 56. (See, Table 9)

TABLE 9

Label Extender of Probe Set derived from the 18S sequence of SEQ ID NO: 3.

| SEQ ID NO: | LABEL EXTENDER NUCLEOTIDE SEQUENCE OF 18S |
|---|---|
| 45 | gataacgaacgagactctggcatTTTTTgaagttaccgtttt |
| 46 | gagcgatttgtctggttaattccTTTTTctgagtcaaagcat |
| 47 | gattccgtgggtggtggtgTTTTTgaagttaccgtttt |
| 48 | gattgacagattgatagctctttctcTTTTTctgagtcaaagcat |
| 49 | caacacgggaaacctcacccTTTTTgaagttaccgtttt |
| 50 | gcctgcggcttaatttgactTTTTTctgagtcaaagcat |
| 51 | ggggagtatggttgcaaagcTTTTTgaagttaccgtttt |
| 52 | ccaaagtctttgggttccggTTTTTctgagtcaaagcat |
| 53 | gaccataaacgatgccgaccTTTTTgaagttaccgtttt |
| 54 | cgatcagataccgtcgtagttccTTTTTctgagtcaaagcat |
| 55 | ccaagaatgttttcattaatcaagaaTTTTTgaagttaccgtttt |
| 56 | ggaccagagcgaaagcatttgTTTTTctgagtcaaagcat |

In another embodiment the probe set comprises a label extender which is designed based on the 28S sequence of SEQ ID NO: 4. Examples of label extenders based on 18S SEQ ID NO: 4 include SEQ ID NOS: 57, 58, 59, 60, 61, 62, 63, 64, 65, 66, 67 and 68. (See, Table 10)

TABLE 10

Label Extender of Probe Set derived from the 28S sequence of SEQ ID NO: 4.

| SEQ ID NO: | LABEL EXTENDER NUCLEOTIDE SEQUENCE OF 28S |
|---|---|
| 57 | catctgtgggattatgactgaacgTTTTTgaagttaccgtttt |
| 58 | gccaatgggcgaagctacTTTTTctgagtcaaagcat |
| 59 | gaaccgcaggttcagacatttTTTTTgaagttaccgtttt |
| 60 | tggtaatcctgctcagtacgagagTTTTTctgagtcaaagcat |
| 61 | cctactgatgatgtgttgttgccaTTTTTgaagttaccgtttt |
| 62 | ccgtcgtgagacaggttagttttacTTTTTctgagtcaaagcat |
| 63 | cgttggattgttcacccactaatagTTTTTgaagttaccgtttt |
| 64 | tgtgaagcagaattcgccaagTTTTTctgagtcaaagcat |
| 65 | tttcagtacgaatacagaccgtgaTTTTTgaagttaccgtttt |
| 66 | caaaagctcgcttgatcttgatTTTTTctgagtcaaagcat |
| 67 | agctcagggaggacagaaaccTTTTTgaagttaccgtttt |
| 68 | cgcaggtgtcctaaggcgTTTTTctgagtcaaagcat |

In another embodiment, the probe set further comprises a blocking label having sequences that hybridize to the generic biomarkers. Examples of blocking label derived from SEQ ID NO: 1 include SEQ ID NO: 69. Examples of blocking label of probe set 2 derived from the Alu sequence of SEQ ID NO: 2 include SEQ ID NOS: 70 and 71. In another embodiment, the probe set comprises a blocking label, which is designed based on the 18S sequence of SEQ ID NO: 3. Examples of blocking label based on 18S SEQ ID NO: 3 include SEQ ID NOS: 72 and 73. In another embodiment the probe set comprises a blocking label is designed based on the 28S sequence of SEQ ID NO: 4. Examples of blocking label based on 28S SEQ ID NO: 4 include SEQ ID NOS: 74, 75, 76 and 77.

TABLE 11

Blocking Label Sequence of Alu Sequences of SEQ ID NOs: 1 and 2, 18S and 28S Sequences.

| SEQ ID NO: | BLOCKING LABEL NUCLEOTIDE SEQUENCES |
|---|---|
| 69 | ggcgcccgccacca |
| 70 | gctcactgcaacctccacct |
| 71 | ggagtgcagtggcatgatcttg |
| 72 | gggcaccaccaggagtgga |
| 73 | ggcgatgcggcggc |
| 74 | cgatgtcggctcttcctatcat |
| 75 | ccacagggataactggcttgtg |
| 76 | aagcaggaggtgtcagaaaagtta |
| 77 | aagcggggcctcacga |

EXAMPLES

Example 1

As shown in FIG. 1, the flow diagram shows the various mechanisms that cause DNA release into the plasma as a result of pathophysiological insults resulting from chemical, radiological or nuclear, biological and explosive exposures.

Example 2

Nucleotide Sequences from which Probe Sets are Designed

Alu Sequence used for Probe Set Design (SEQ ID NO: 1)

AGACCATCCTGGCTAACACGGTGAAACCCCGTCTCTACTAAAAATACAAA
AAATTAGCCGGGCGTGGTGGCGGGCGCCTGTAGTCCCAGCTACTCGGGAG
GCTGAGGCAGGAGAATGGCGTGAACCCGGGAGGCGGAGCTTGCAGTGAGC
CGAGATCGCGCCACTGCACTCCAGCCTGGG CGACAGAGCGAGACTCCGT
CT

Alu Sequence used for Probe Set Design (SEQ ID NO: 2)

AGACCATCCTGGCTAACACGGTGAAACCCCGTCTCTACTAAAAATACAAA
AAATTAGCCGGGCGTGGTGGCGGGCGCCTGTAGTCCCAGCTACTCGGGAG
GCTGAGGCAGGAGAATGGCGTGAACCCGGGAGGCGGAGCTTGCAGTGAGC
CGAGATCGCGCCACTGCACTCCAGCCTGGGCGACAGAGCGAGACTCCGTC
T

18S Sequence used for Probe Set Design (SEQ ID NO: 3)

ATGCCAGAGTCTCGTTCGTTATCGGAATTAACCAGACAAATCGCTCCACC
AACTAAGAACGGCCATGCACCACCACCCACGGAATCGAGAAAGAGCTATC
AATCTGTCAATCCTGTCCGTGTCCGGGCCGGGTGAGGTTTCCCGTGTTGA
GTCAAATTAAGCCGCAGGCTCCACTCCTGGTGGTGCCCTTCCGTCAATTC
CTTTAAGTTTCAGCTTTGCAACCATACTCCCCCCGGAACCCAAAGACTTT
GGTTTCCCGGAAGCTGCCCGGCGGGTCATGGGAATAACGCCGCCGCATCG
CCGGTCGGCATCGTTTATGGTCGGAACTACGACGGTATCTGATCGTCTTC
GAACCTCCGACTTTCGTTCTTGATTAATGAAAACATTCTTGGCAAATGCT
TTCGCTCTGGTCC

28S Sequence used for Probe Set Design (SEQ ID NO: 4)

CGTTCAGTCATAATCCCACAGATGGTAGCTTCGCCCCATTGGCTCCTCAG
CCAAGCACATACACCAAATGTCTGAACCTGCGGTTCCTCTCGTACTGAGC
AGGATTACCATGGCAACAACACATCATCAGTAGGGTAAAACTAACCTGTC
TCACGACGGTCTAAACCCAGCTCACGTTCCCTATTAGTGGGTGAACAATC
CAACGCTTGGCGAATTCTGCTTCACAATGATAGGAAGAGCCGACATCGAA
GGATCAAAAAGCGACGTCGCTATGAACGCTTGGCCGCCACAAGCCAGTTA
TCCCTGTGGTAACTTTTCTGACACCTCCTGCTTAAAACCCAAAAGGTCAG
AAGGATCGTGAGGCCCCGCTTTCACGGTCTGTATTCGTACTGAAAATCAA
GATCAAGCGAGCTTTTGCCCTTCTGCTCCACGGGAGGTTTCTGTCCTCCC
TGAGCTCGCCTTAGGACACCTGCG

Telomeric Sequence used for Probe Set Design

TTAGGG          (SEQ ID NO: 5)
TTTTGGGG        (SEQ ID NO: 6)

Example 3

Protocol for QuantiGene™ Detection Method

Figure 2:
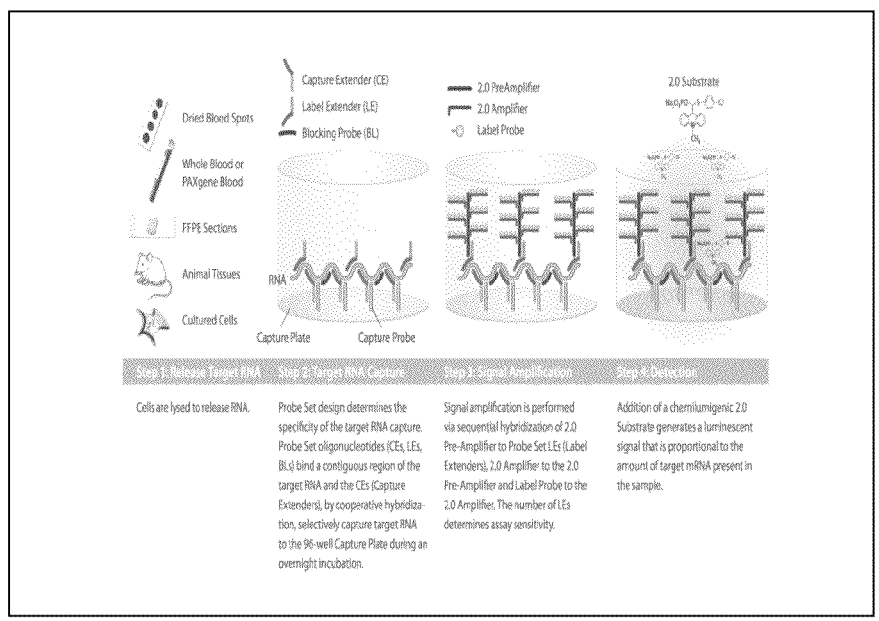
FIG. 2 shows the schematic for detecting DNA released into the circulation as a result of pathophysiological insults.

As shown in FIG. 2, the schematic shows the method of detection being carried out using the QuantiGene™ method. Briefly, the method involves capturing target circulating DNA from a plasma sample by mixing probe set comprising both the capture extender and label extender with the plasma sample under hybridizing conditions at 55° C. for 30 minutes in 3×SSC, 10% dextransulfate, 0.2% casein, 10 ug/ml polyA and 100 ug/ml denatured salmon sperm DNA. Signal amplification is then carried out by sequentially hybridizing pre-Amplifier, Amplifier and Label Probe at 55° C., 55° C. and 50° C. respectively for 10 minutes each in 3×SSC, 10% dextransulfate, 0.2% casein, 10 ug/ml polyA and 100 ug/ml denatured salmon sperm DNA and with wash buffer: 20 mmol/L Tris-HCL, 400 mmol/L lithium chloride, 1 mL/L Tween 20. The Label Probe may be biotinylated.

Example 4

Correlation of Relative Light Units (RLU) with Alu Sequence Concentration

Samples containing various concentrations of Alu sequences were incubated with Capture Probe-coated plates together with Alu-specific Capture Extender (CE), Label Extender (LE) and Blocking Label (BL) for 1, 2, 3, 4 h and overnight.

Example 5

Detection of Plasma DNA Over a 24-h Period Following Total Body Irradiation

As shown in FIG. 4, an exemplary experiment showing the detection of plasma DNA following total body irradiation in mice. Mice were irradiated with 10 Gy of radiation with $Ce^{137}$ irradiator at dose rate of 1.83 Gy/min. At 0, 3, 6, 9, 12 and 24 hours following irradiation, plasma samples were taken from the mice and diluted at 1:10 with distilled water. Two, five, ten and twenty μL of the diluted samples were taken for analysis following the protocol described in Example 2 above. Free plasma DNA released from the cells as a result of damage due to radiation exposure was measured using probe set containing Alu sequences:

Mouse Probeset:

```
B4gaInt2_alu.29.45.CE    CE  tgcctcccgagtgctggTTTTTctcttggaaagaaagt
                             SEQ ID NO.: 78

B4gaInt2_alu.46.65.CE    CE  ctcagaaatccgcctgcctcTTTTTctcttggaaagaaagt
                             SEQ ID NO.: 79

B4gaInt2_alu.66.84.CE    CE  agaccaggctggcctcgaaTTTTTctcttggaaagaaagt
                             SEQ ID NO.: 80

B4gaInt2_alu.108.129.CE CE   agacagggtttctctgtagcccTTTTTctcttggaaagaaagt
                             SEQ ID NO.: 81

B4gaInt2_alu.8.28.LE     LE  gattaaaggcatgcaccaccaTTTTTctgagtcaaagcatgaagttac
                             SEQ ID NO.: 82

B4gaInt2_alu.85.107.LE   LE  tggtgtcctggaactcactctgaTTTTTctgagtcaaagcatgaagttac
                             SEQ ID NO.: 83
```

Mouse Seq:

```
>B4gaInt2_alu
CCGGGCATGGTGGTGCATGCCTTTAATCCCAGCACTCGGGAGGCAGAGGC
AGGCGGATTTCTGAGTTCGAGGCCAGCCTGGTCTTCAGAGTGAGTTCCAG
GACACCAGGGCTACAGAGAAACCCTGTCT
SEQ ID NO.: 84
```

Figure 4A:
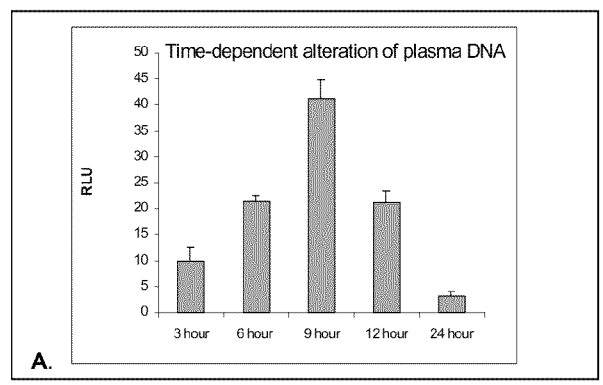
FIG. 4A shows DNA released into the circulation after total body irradiation of 10 Gy. over a 24-hour period.

The results in FIG. 4A showed an increase in plasma DNA from a 5 μL of 1:10 diluted samples over time using the method described in the present invention. The amount of free plasma DNA peaked at 9 h post irradiation.

Figure 4B:
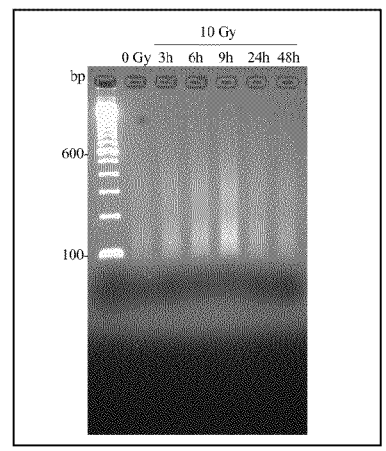
FIG. 4B shows ethidium bromide stained DNA of samples FIG. 3A above.

FIG. 4B confirmed the results obtained by running the samples in a 2% agarose gel followed by staining with ethidium bromide.

Example 6

Free DNA Released into Plasma Increased with Radiation Dose

Figure 5:
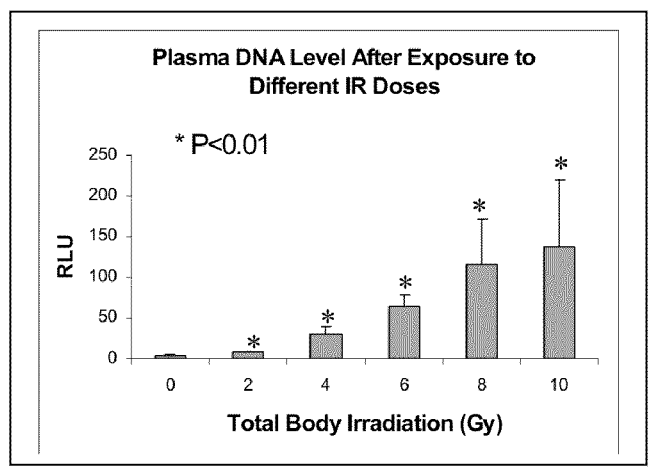
FIG. 5 shows the correlation between DNA released into the circulation and radiation dose.

The radiation dose response measuring the amount of free circulating generic biomarker, using the Alu-like sequence in mice (the B1 sequence) and the appropriate sequence probe set and the QuantiGene™ method of detection described in Example 2 above is shown in FIG. 5. Plasma samples were obtained from mice 9 h post total body irradiation with gamma radiation generated by a 137Cs source at 0, 2, 4, 6, 8, and 10 Gy. The amount of free circulating Alu biomarker released into the plasma were measured using the QuantiGene™ detection method described in Example 2 above with Alu sequence probe set Mouse Probeset:

```
B4gaInt2_alu.29.45.CE    CE  tgcctcccgagtgctggTTTTTctcttggaaagaaagt
                             SEQ ID NO.: 78

B4gaInt2_alu.46.65.CE    CE  ctcagaaatccgcctgcctcTTTTTctcttggaaagaaagt
                             SEQ ID NO.: 79

B4gaInt2_alu.66.84.CE    CE  agaccaggctggcctcgaaTTTTTctcttggaaagaaagt
                             SEQ ID NO.: 80

B4gaInt2_alu.108.129.CE CE   agacagggtttctctgtagcccTTTTTctcttggaaagaaagt
                             SEQ ID NO.: 81
```

```
B4gaInt2_alu.8.28.LE     LE  gattaaaggcatgcaccaccaTTTTTctgagtcaaagcatgaagttac
                             SEQ ID NO.: 82

B4gaInt2_alu.85.107.LE   LE  tggtgtcctggaactcactctgaTTTTTctgagtcaaagcatgaagttac
                             SEQ ID NO.: 83
```

Mouse Seq:

```
>B4gaInt2_alu
CCGGGCATGGTGGTGCATGCCTTTAATCCCAGCACTCGGGAGGCAGAGGC

AGGCGGATTTCTGAGTTCGAGGCCAGCCTGGTCTTCAGAGTGAGTTCCAG

GACACCAGGGCTACAGAGAAACCCTGTCT
SEQ ID NO.: 84
```

The results showed that the amount of free plasma DNA measured using the Alu sequences, released into circulation increased with increase radiation dose. Statistical analysis showed that even at lower doses of 2, 4, and 6 Gy, a significant difference (P<0.05) can be detected between the different radiation dose and background DNA levels in un-irradiated mice (healthy mice) can be distinguished. The results also show that the generic biomarker used in this assay was sufficiently sensitive for detection of radiation exposure within 9 h of exposure.

Example 7

Sub-Acute and Latent Effect is Dependent on Radiation Dose

Figure 6:
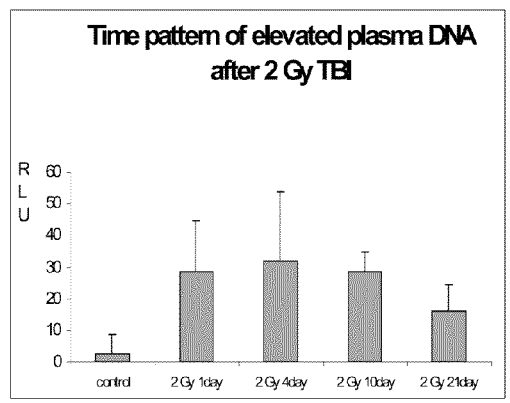
FIG. 6 shows DNA released into the circulation after total body irradiation of 2 and 5 Gy over a 21-day period.
Figure 6:
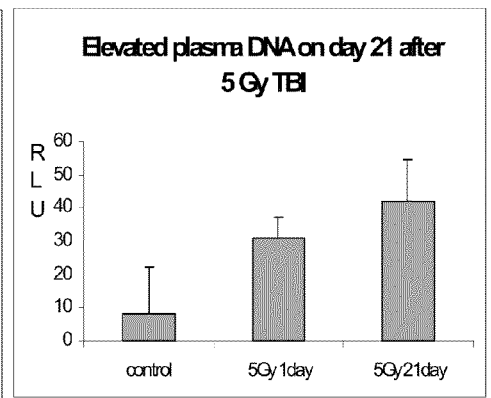

The time course for free plasma DNA in the circulation was shown in FIG. 6 to illustrate the sub-acute and latent effects of two different radiation doses measured over time following total body irradiation of mice (2 and 5 Gy using gamma radiation from a 137Cs source Free plasma DNA was measured using the QuantiGene™ method of detection described in Example 2
Mouse Probeset:

```
B4gaInt2_alu.29.45.CE    CE  tgcctcccgagtgctggTTTTTctcttggaaagaaagt
                             SEQ ID NO.: 78

B4gaInt2_alu.46.65.CE    CE  ctcagaaatccgcctgcctcTTTTTctcttggaaagaaagt
                             SEQ ID NO.: 79

B4gaInt2_alu.66.84.CE    CE  agaccaggctggcctcgaaTTTTTctcttggaaagaaagt
                             SEQ ID NO.: 80

B4gaInt2_alu.108.129.CE  CE  agacagggtttctctgtagcccTTTTTctcttggaaagaaagt
                             SEQ ID NO.: 81

B4gaInt2_alu.8.28.LE     LE  gattaaaggcatgcaccaccaTTTTTctgagtcaaagcatgaagttac
                             SEQ ID NO.: 82

B4gaInt2_alu.85.107.LE   LE  tggtgtcctggaactcactctgaTTTTTctgagtcaaagcatgaagttac
                             SEQ ID NO.: 83
```

Mouse Seq:

```
>B4gaInt2_alu
CCGGGCATGGTGGTGCATGCCTTTAATCCCAGCACTCGGGAGGCAGAGGC

AGGCGGATTTCTGAGTTCGAGGCCAGCCTGGTCTTCAGAGTGAGTTCCAG

GACACCAGGGCTACAGAGAAACCCTGTCT
SEQ ID NO.: 84
```

As shown in FIG. 6A, in plasma of mice exposed to 2 Gy radiation, the amount of free DNA detected in the circulation decreased two-fold 21-days after irradiation. On the other hand in FIG. 6B, mice exposed to 5 Gy irradiation continued to increase in the amount of free plasma DNA in the circulation 21-days after irradiation. The results show that the levels of free plasma DNA can be used to predict the level of damage to the cells following radiation exposure and the method described in the present invention can be used to monitor the course of the damage resulting from pathophysiological insults such as that caused by radiation.

Example 8

Increased Free Plasma DNA Levels Detected in Different Disease States

The plasma was taken from the same plasma tube of patients who was diagnosed as MI according to the elevated plasma CK-MB, and then tested with human Alu kit. A close correlation was observed.

Human plasma samples were collected and 10 ul of plasma was used for each test. Probe sets are list below.

| SEQ ID NO: | CAPTURE EXTENDER NUCLEOTIDE SEQUENCE OF PROBE SET 1 |
|---|---|
| 7 | attttagtagagacggggtttcaTTTTTctcttggaaagaaagt |
| 8 | cgcccggctaattttttgtTTTTTctcttggaaagaaagt |

| SEQ ID NO: | CAPTURE EXTENDER NUCLEOTIDE SEQUENCE OF PROBE SET 1 |
|---|---|
| 9 | cgcctcccgggttcacgTTTTTctcttggaaagaaagt |
| 10 | ggagtgcagtggcgcgaTTTTTctcttggaaagaaagt |
| 11 | cgctctgtcgcccaggctTTTTTctcttggaaagaaagt |

| SEQ ID NO: | LABEL EXTENDER NUCLEOTIDE SEQUENCE OF PROBE SET 1 |
|---|---|
| 32 | ccgtgttagccaggatggtctTTTTTctgagtcaaagcatgaagttac |
| 33 | tcccgagtagctgggactacaTTTTTctgagtcaaagcatgaagttac |
| 34 | ccattctcctgcctcagccTTTTTctgagtcaaagcatgaagttac |
| 35 | tctcggctcactgcaagctcTTTTTctgagtcaaagcatgaagttac |

| SEQ ID NO: | BLOCKING LABEL NUCLEOTIDE SEQUENCES |
|---|---|
| 69 | ggcgcccgccacca |
| 70 | gctcactgcaacctccacct |
| 71 | ggagtgcagtggcatgatcttg |
| 72 | gggcaccaccaggagtgga |
| 73 | ggcgatgcggcggc |
| 74 | cgatgtcggctcttcctatcat |
| 75 | ccacagggataactggcttgtg |

| SEQ ID NO: | CAPTURE EXTENDER NUCLEOTIDE SEQUENCE OF PROBE SET 1 |
|---|---|
| 7 | attttagtagagacggggtttcaTTTTTctcttggaaagaaagt |
| 8 | cgcccggctaattttttgtTTTTTctcttggaaagaaagt |
| 9 | cgcctcccgggttcacgTTTTTctcttggaaagaaagt |
| 10 | ggagtgcagtggcgcgaTTTTTctcttggaaagaaagt |
| 11 | cgctctgtcgcccaggctTTTTTctcttggaaagaaagt |

| SEQ ID NO: | LABEL EXTENDER NUCLEOTIDE SEQUENCE OF PROBE SET 1 |
|---|---|
| 32 | ccgtgttagccaggatggtctTTTTTctgagtcaaagcatgaagttac |
| 33 | tcccgagtagctgggactacaTTTTTctgagtcaaagcatgaagttac |
| 34 | ccattctcctgcctcagccTTTTTctgagtcaaagcatgaagttac |
| 35 | tctcggctcactgcaagctcTTTTTctgagtcaaagcatgaagttac |

-continued

| SEQ ID NO: | BLOCKING LABEL NUCLEOTIDE SEQUENCES |
|---|---|
| 76 | aagcaggaggtgtcagaaaagtta |
| 77 | aagcggggcctcacga |

Figure 7:
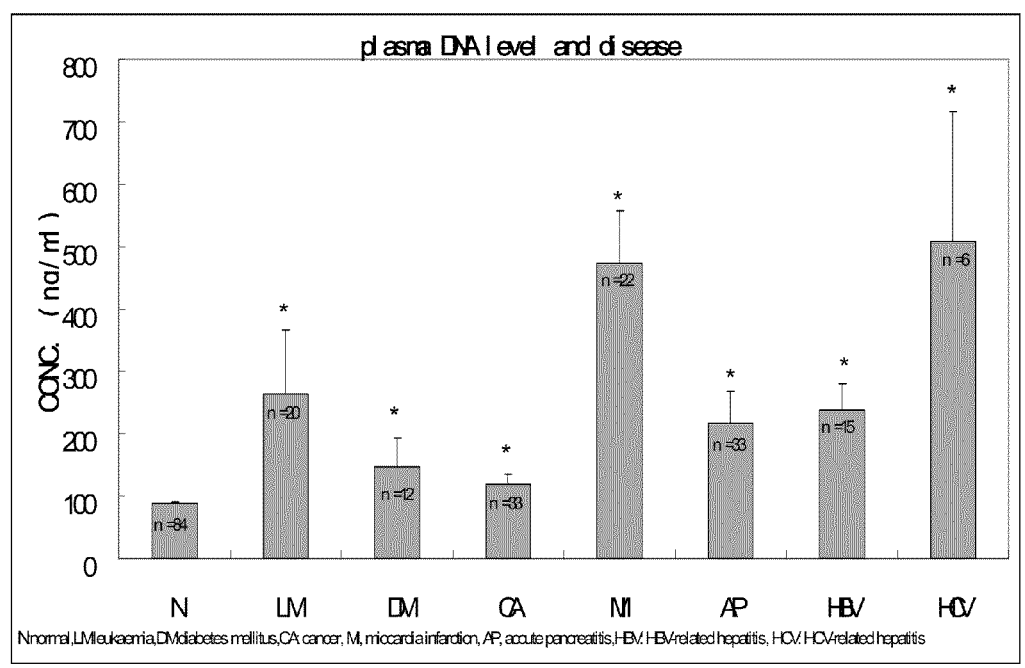
FIG. 7 shows DNA released into the circulation for various disease states.

As shown in FIG. 7, the levels of free plasma DNA was shown to be higher in samples obtained from human subjects with leukemia (LM), diabetes mellitus (DM), cancer (CA), myocardia infarction (M), acute pancreatitis (AP), HBV (hepatitis B), and HCV (hepatitis C) as compare to the level of free plasma DNA in samples from healthy individuals (N).

Example 9

Free Plasma DNA Levels Correlates with Levels of Creatine Kinase 2 (CK-MB) in Patient with Myocardia Infarction The plasma was taken from the same plasma tube of patients who was diagnosed as MI according to the elevated plasma CK-MB, and then tested with human Alu kit. A close correlation was observed.

Human plasma samples were collected and 10 ul of plasma was used for each test. Probe sets are list below.

| SEQ ID NO: | BLOCKING LABEL NUCLEOTIDE SEQUENCES |
|---|---|
| 69 | ggcgcccgccacca |
| 70 | gctcactgcaacctccacct |
| 71 | ggagtgcagtggcatgatcttg |
| 72 | gggcaccaccaggagtgga |
| 73 | ggcgatgcggcggc |
| 74 | cgatgtcggctcttcctatcat |
| 75 | ccacagggataactggcttgtg |
| 76 | aagcaggaggtgtcagaaaagtta |
| 77 | aagcggggcctcacga |

Figure 8:
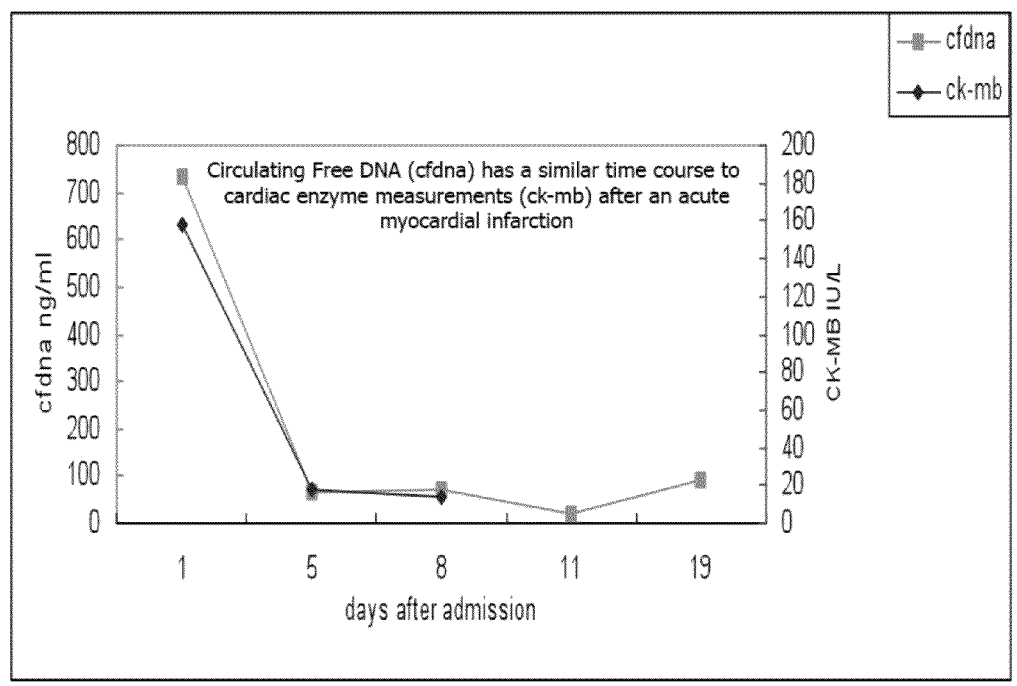
FIG. 8 shows the correlation between DNA released into the circulation and the presence of creatine-kinase 2 (CK-MB) in a patient with myocardia infarction.

The results in FIG. 8 showed that the amount of free plasma DNA released into the circulation correlated with the presence of creatine kinase 2 (CK-MB) in patient with myocardia infarction. Furthermore, the results also show that that the assay is just as reliable as the well-established assay using CK-MB for detection of myocardia infarction.

Example 10

Treatment with D68, a Radio-Protective Agent Reduces Free Plasma DNA in the Circulation of Irradiated Mice BALB/c mice (5 per group) exposed to total body irradiation of 10 Gy (gamma irradiation from a 137Cs source) were treated with saline (control) and 350 mg/kg of D68, a radio-protective agent (University of Rochester, N.Y., Department of Radiation Oncology). International Patent Application No. PCT/US2008/064872. Based on U.S. Provisional Patent Application No. 60/940,396, the patent application is herein incorporated by reference. Plasma samples from the mice were collected 9-h post-irradiation and the amount of free plasma DNA present in circulation is measured using the QuantiGene™ method of detection described in Example 2 using the Alu-like B1 sequence derived probe set of human Alu probe set.

Figure 9:
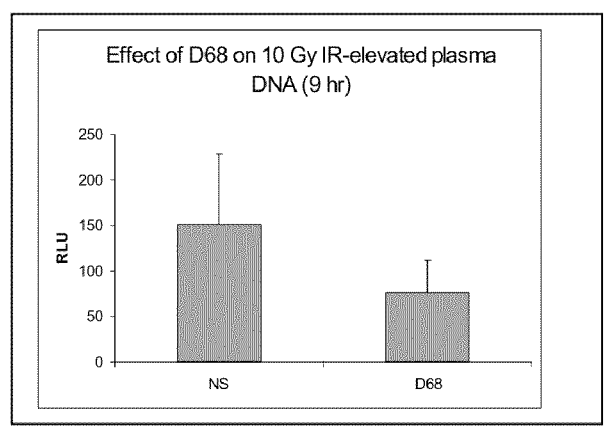
FIG. 9 shows the effect of D68, a radio-protective agent used for protecting/treating a subject from the effects of radiation.

FIG. 9 showed the effect of D68, a radio-protective agent on the levels of free plasma DNA in the circulation of irradiated mice treated with D68 as compared to saline-treated control mice (NS). Irradiated mice treated with D68 had reduced levels of free plasma Alu DNA in the circulation compared to irradiated mice treated with saline, consistent with their lowered sensitivity to irradiation due to the agent.

All publications, patents and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A method for predicting the level of damage to cells in a mammal, comprising:
    a) measuring hybridization of an Alu repeat-specific oligonucleotide probe with nucleic acid that is in a sample of blood plasma that has been obtained from a mammal that has been exposed to radiation, wherein said measuring provides the level of free circulating Alu nucleic acid in the bloodstream of said mammal and said measuring is done without amplifying said free circulating Alu nucleic acid from said blood plasma; and
    b) predicting the level of damage to cells in said mammal using said level of free circulating Alu nucleic acid, wherein there is a positive correlation between increased free circulating Alu nucleic acid and increased dose of radiation.

2. The method of claim 1, wherein said mammal has been exposed to radiation produced by a nuclear accident.

3. The method of claim 1, wherein said mammal has been exposed to radiation produced by a dirty bomb.

4. The method of claim 1, wherein said mammal has been exposed to radiation produced by a nuclear bomb.

5. The method of claim 1, wherein said mammal has been exposed to gamma radiation.

6. The method of claim 1, wherein said mammal is a human.

7. The method of claim 1, wherein, prior to said measuring, said mammal has been administered with a radio-protective agent for protecting and/or treating said mammal from the effects of radiation.

8. The method of claim 1, wherein the level of said nucleic acid is measured by:
    a) hybridizing said nucleic acid with an Alu-specific oligonucleotide that is attached to a solid support; and
    b) detecting the Alu-containing nucleic acid captured by said Alu-specific oligonucleotide, directly or indirectly, using a branched nucleic acid.

9. The method of claim 1, wherein said method comprises measuring the level of said free circulating Alu nucleic acid over a timecourse.

10. The method of claim 9, wherein said method comprises calculating the rate of increase of said free circulating Alu nucleic acid.

11. The method of claim 9, wherein said method comprises calculating the peak level of said free circulating Alu nucleic acid.

12. The method of claim 1, wherein said method further comprises predicting the level of damage to cells in said mammal using the level of free circulating 18S DNA, 28S DNA and/or telomere DNA in the bloodstream of said mammal.

* * * * *